(12) United States Patent
Konishi et al.

(10) Patent No.: US 9,351,947 B2
(45) Date of Patent: May 31, 2016

(54) USE OF CATECHOLAMINES AND RELATED COMPOUNDS AS ANTI-ANGIOGENIC AGENTS

(75) Inventors: Yasuo Konishi, Kirkland (CA); Joanne Magoon, Montreal (CA); Suwatchai Jarussophon, Montreal (CA)

(73) Assignee: National Research Council of Canada, Ottawa, Ontario (\*) Notice: Subject to any disclaimer, the term of this patent is extended or adjusted under 35 U.S.C. 154(b) by 1636 days.

(21) Appl. No.: 12/448,981

(22) PCT Filed: Jan. 29, 2008

(86) PCT No.: PCT/CA2008/000191
§ 371 (c)(1),
(2), (4) Date: Jul. 17, 2009

(87) PCT Pub. No.: WO2008/092257
PCT Pub. Date: Aug. 7, 2008

(65) Prior Publication Data
US 2010/0069401 A1    Mar. 18, 2010

Related U.S. Application Data

(60) Provisional application No. 60/897,814, filed on Jan. 29, 2007, provisional application No. 60/924,574, filed on May 25, 2007.

(51) Int. Cl.
| | | |
|---|---|---|
| *A61K 31/137* | (2006.01) | |
| *A61K 31/216* | (2006.01) | |
| *A61K 31/222* | (2006.01) | |
| *A61K 31/36* | (2006.01) | |
| *A61K 31/445* | (2006.01) | |
| *A61K 31/495* | (2006.01) | |
| *A61K 31/522* | (2006.01) | |

(52) U.S. Cl.
CPC ............. *A61K 31/137* (2013.01); *A61K 31/216* (2013.01); *A61K 31/222* (2013.01); *A61K 31/36* (2013.01); *A61K 31/445* (2013.01); *A61K 31/495* (2013.01); *A61K 31/522* (2013.01)

(58) Field of Classification Search
CPC ............................ A61K 31/137; C07C 215/60
See application file for complete search history.

(56) References Cited

U.S. PATENT DOCUMENTS

| | | | |
|---|---|---|---|
| 3,885,047 A | | 5/1975 | Seidehamel et al. |
| 3,985,897 A | * | 10/1976 | Seidehamel et al. .......... 514/605 |
| 5,395,970 A | | 3/1995 | Tuttle et al. |
| 2003/0181354 A1 | | 9/2003 | Abdulrazik |
| 2004/0038972 A1 | | 2/2004 | Den Hartog et al. |
| 2005/0043408 A1 | | 2/2005 | Yeboah et al. |
| 2007/0112076 A1 | | 5/2007 | Steine |

FOREIGN PATENT DOCUMENTS

| | | |
|---|---|---|
| WO | 96/06081 | 2/1996 |
| WO | 03/032969 | 4/2003 |

(Continued)

OTHER PUBLICATIONS

Kliffen et al. (British Journal of Ophthalmology, vol. 81, pp. 154-162; 1997).*

(Continued)

*Primary Examiner* — Leslie A. Royds Draper
(74) *Attorney, Agent, or Firm* — Sonia Patenaude

(57) ABSTRACT

A catecholamine or related compound having (S)-configuration at β-carbon, a physiologically tolerated salt thereof, a prodrug thereof, a physiologically functional derivative thereof or any mixture thereof and having a lipophilicity greater than (S)-noradrenaline has use as an anti-angiogenic agent. A catecholamine or related compound in which a β-hydroxy group has been modified are also anti-angiogenic. The anti-angiogenic agent is preferably a compound of formula (I) or (II)

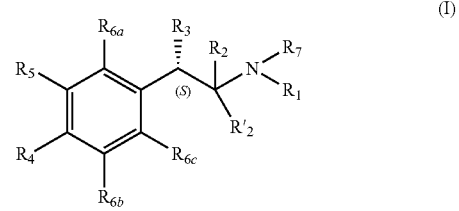

(I)

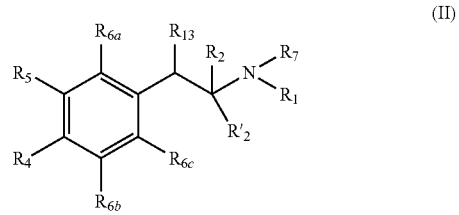

(II)

a physiologically tolerated salt thereof, a prodrug thereof, a physiologically functional derivative thereof or any mixture thereof.

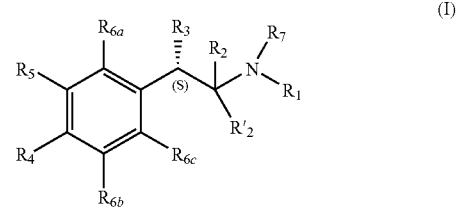

(I)

8 Claims, 10 Drawing Sheets

(56) References Cited

FOREIGN PATENT DOCUMENTS

| WO | 2006/015830 | 2/2006 |
|---|---|---|
| WO | 2007/109882 | 10/2007 |

OTHER PUBLICATIONS

Corey et al. (Tetrahedron Letters, vol. 31, Issue 5, abstract; 1990).*
Mack et al. (Naunyn-Schmiedeberg's Arch. Pharmacol., vol. 310, pp. 1-9; 1979).*
Stella (Expert Opinion on Therapeutic Patents, Prodrugs as therapeutics, vol. 14, No. 3, pp. 277-280; 2004).*
Wolff (Burger's Medicinal Chemistry, 5th Ed., vol. 1, pp. 975-977; 1994).*
Testa (Biochemical Pharmacology, Prodrug Research: futile or fertile?, vol. 68, pp. 2097-2106; 2004).*
Ettmayer et al. (Medicinal Chemistry, Lessons Learned from Marketed and Investigational Prodrugs, vol. 47, No. 10, pp. 2394-2404; 2004).*
Hida et al. (Cancer Sci, vol. 99, No. 3, abstract; 2008).*
STN Registry No. 2964-04-7. "(S)-Isoproterenol". STN Registry File. Retrieved May 8, 2014. One page.*
Amano, H; et al. (2001) Adenylate Cyclase / Protein Kinase A Signaling Pathway EnhancesAngiogenesis Through Induction of Vascular Endothelial Growth Factor In Vivo. Jpn. J. Pharmacol. 87, 181-188.
Basu, S.; Nagy, J. A.; Pal, S.; Vasile, E.; Eckelhoefer, I. A.; Bliss, V. S.; Manseau, E. J.; Dasgupta, P. S.; Dvorak, H. F.; Mukhopadhyay, D. The neurotransmitter dopamine inhibits angiogenesis induced by vascular permeability factor/vascular endothelial growth factor. Nat. Med. (2001), 7, 569-574.
Bentley, G. A.; Starr, J. The antinociceptive action of some β-adrenoceptor agonists in mice. Br. J. Pharmacol. (1986) 88, 515-521.
Boulton, D. W.; Fawcett, J. P. β2-Agonist eutomers: A rational option for the treatment of asthma? Am. J. Respir. Med. (2002), 1, 305-311.
Chalothom, D.; Zhang, H.; Clayton, J.A.; Thomas, S.A.; Faber, J.E. Catecholamines augment collateral vessel growth and angiogenesis in hindlimb ischemia. Am. J. Physiol. Heart Circ. Physiol. (2005) 289, H947-H959.
Chen, A. S.; Taguchi, T.; Sugiura, M.; Wakasugi, Y.; Kamei, A.; Wang, M. W.; Miwa, I. Pyridoxal-aminoguanidine adduct is more effective than aminoguanidine in preventing neuropathy and cataract in diabetic rats. Horm. Metab. Res. (2004) 36, 183-187.
Conway, W. D.; Minatorya, H.; Lnds, A. M.; Shekosky, J. M. Absorption and elimination profile of isoproterenol III. The metabolic fate of dl-isoproterenol-7-3H in the dog. J. Pharm. Sci. (1968) 57, 1135-1141.
Corey E.J. et al. (1990) The First Enantioselective Syntheses of Pure R- and S-Isoproterenol, Tetrahedron Letters, vol. 31, No. 5, pp. 601-604.
Dejgaard, A.; Hilsted, J.; Christensen, N.J. Noradrenaline and isoproterenol kinetics in diabetic patients with and without autonomic neuropathy. Diabetologia. (1986) 29, 773-777.
Ettmayer P, et al. (2004) Lessons Learned from Marketed and Investigational Prodrugs, Journal of Medicinal Chemistry, vol. 47, No. 10, 2393-2404.
Hida, K. et al. (2008) Understanding tumor endothelialcel abnormalities to develop ideal anti-angiogenic therapies. Cancer Sci. Mar. 99 (3) 459-66.
Infeld, D. (1998) Diabetic Retinopathy. Postgrad Med. J.. 74:129-133.
ISR/WO dated Apr. 18, 2008 on corresponding PCT application PCT/CA2008/000191.
Jarvinen, T.; Jarvinen, K. Prodrugs for improved ocular drug delivery. Adv. Drug Delivery Rev. (1996), 19, 203-224.
Kass, M. A.; Reid, T. W.; Neufeld, A. H.; Bausher, L. P.; Sears, M. L. The effect of d-isoproterenol on intraocular pressure of the rabbit, monkey, and man. Invest. Ophthalmol. (1976), 15, 113-118.
Kliffen, M. et al. (1997) Increased expression of angiogenic growth factors in age related maculopathy. British Journal of Ophthalmology. 81:154-162.
Kyselova, Z.; Stefek, M.; Bauer, V. Pharmacological prevention of diabetic cataract. J. Diabetes Complications. (2004) 18, 129-140.
Lands, A. M.; Luduena, F. P.; Tullar, B. F. The pharmacologic activity of the optical isomers of isoproterenol compared with that of the optically inactive analog 1-(3,4-dihydroxyphenyl)-2-isopropylaminoethane HCI. J. Pharmacol. Exp. Ther. (1954), 111, 469-474.
Mack, F. et al. (1979) Dissociation Constants and Lipophilicity of Catecholamines and related compounds. Naunyn-Schmiedeberg's Arch. Pharmacol 310, 1-9.
Mandell, A. I.; Stentz, F.; Kitabchi, A. E. Dipivalyl epinephrine: a new pro-drug in the treatment of glaucoma. Ophthalmology. (1978) 85, 268-275.
Moshfeghi, D. (2003) Age-related macular degeneration: Evaluation and Treatment. Cleveland Clinic Journal of Medicine. vol. 70, No. 12, 1017-1037.
Neufeld, A. (1977) In vitro determination of the ability of drugs to bind to adrenergic receptors. Invest. Ophthalmol. Visual Sci. vol. 16, No. 12, 1118-1124.
Patil, P. N.; Miller, D. D.; Trendelenburg U. Molecular geometry and adrenergic drug activity. Pharmacol. Rev. (1974), 26, 323-392.
Ross, R. A.; Drance, S. M. Effects of topically applied isoproterenol on aqueous dynamics in man. Arch. Ophthal. (1970) 83, 39-46.
Sakurai, S. et al. (2002) Retinal Capillary Pericyte Proliferation and c-Fos mRNA Induction by Prostaglandin D2 through the cAMP Response Element. Investigative Ophthalmology & Visual Science, vol. 43, No. 8, 2774-2781.
Seidehamel, R. J.; Dungan, K. W.; Hickey, T. E. Specific hypotensive and antihypertensive ocular effects of d-isoproterenol in rabbits. Am. J. Ophthalmol. (1975), 79, 1018-1025.
Stella, V.J. (2004) Prodrugs as Therapeutics. Expert Opinion on Therapeutic Patents. vol. 14, No. 3, pp. 277-280.
Testa, B. (2004) Prodrug research: futile or fertile? Biochemical Pharmacology 68. 2097-2106.
Thaker,P.H.; Han,L. Y.; Kamat, A. A.; Arevalo, J. M.; Takahashi, R.; Lu, C.; Jennings, N. B.; Armaiz-Pena, G.; Bankson, J. A.; Ravoori, M.; Merritt, W. M.; Lin, Y. G.; Mangala, L. S.; Kim, T. J.; Coleman, R. L.; Landen, C. N.; Yang Li, Y.; Felix, E.; Sanguino, A. M.; Newman, R. A.; Lloyd, M.; Gershenson, D. M.; Kundra, V.; Lopez-Berestein, G.; Lutgendorf, S. K.; Cole, S. W.; Sood, A. K. Chronic stress promotes tumor growth and angiogenesis in a mouse model of ovarian carcinoma. Nat. Med. (2006), 12, 939-944.
Walker, S. B.; Kradjan, W. A.; Bierman, C. W. Bitolterol mesylate: a beta-adrenergic agent. Chemistry, pharmacokinetics, pharmacodynamics, adverse effects and clinical efficacy in asthma. Pharmacotherapy (1985), 5, 127-137.
Wang, B. C.; Bloxham, D. D.; Goetz, K. L. Effect of dipivalyl derivatives of catecholamines on cardiovascular function in the conscious dog. J. Pharmacol. Exp. Ther. (1977) 203, 442-448.
Wolf, M. (1994) Burger's Medicinal Chemistry and Drug Discovery, 5th Ed. vol. 1: Principles and Practices. 975-977.
Abstract of JP 9 136830 (Kagaku Gijutsu Shinko Jigyodan) May 27, 1997 "Isoproterenol-containing retina protectant is useful for treating diseases causing injury to retinal cells e.g. diabetes mellitus. etc". XP002228062.
Office action dated May 28, 2012 on corresponding Australian Application 2008210237.
Extended European Search Report dated Jun. 5, 2012 on corresponding European application 08706338.4.
Johnson K, et al. "Metabolism, Pharmacokinetics, and Excretion of a Highly Selective N-Methyl-D-Aspartate Receptor Antagonist, Traxoprodil, in Human Cytochrome P450 2d6 Extensive and Poor Metabolizers". Drug Metabolism and Disposition. vol. 31, No. 1, Jan. 1, 2003 pp. 76-87. XP009069857.
Comai K, et al. "Phenethylamine Inhibitors of Partially Purified Rat and Human Pancreatic Lipase". Journal of Pharmaceutical Sciences. vol. 71. No. 4. 1982. pp. 418-421. XP007920652.
Pandya NM, et al. "Angiogenesis—a new target for future therapy." Vascular Pharmacology. vol. 44. No. 5. May 1, 2006, pp. 265-274. XP024970442.

(56) References Cited

OTHER PUBLICATIONS

Rhodia. "GPS Safety Summary Para-trifluoromethylaniline". Dec. 1, 2011. XP007920651.

Nagarajan et al. "A novel catecholamine, arbutamine, for a pharmacological cardiac stress agent". Cardiovascular Drugs and Therapy. vol. 10, No. 1, Jan. 1, 1996, pp. 31-38. XP009159647.

* cited by examiner

Control (S)-Isoproterenol

USE OF CATECHOLAMINES AND RELATED COMPOUNDS AS ANTI-ANGIOGENIC AGENTS

CROSS-REFERENCE TO RELATED APPLICATIONS

This application is a national entry of International Application PCT/CA2008/000191 filed Jan. 29, 2008 and claims the benefit of U.S. Provisional Patent Applications Ser. No. 60/897,814 filed Jan. 29, 2007 and U.S. Ser. No. 60/924,674 filed May 25, 2007, the entire contents of all of which are herein incorporated by reference.

FIELD OF THE INVENTION

This invention relates to the use of catecholamines and related compounds as anti-angiogenic agents to prevent and/or treat angiogenesis and related diseases.

BACKGROUND OF THE INVENTION

Angiogenesis is a physiological process involving the growth of new blood vessels from pre-existing vessels through endothelial cell proliferation and migration with remodeling of the extracellular matrix. It is a normal process in organ development and differentiation during embryogenesis, in wound healing, and in the uterus and ovary. It is also involved in pathogenic disorders such as diabetic retinopathy, diabetic macular edema, age-related macular degeneration, ischemic heart disorders, rheumatoid arthritis, psoriasis, tumorigenesis and tumor growth.

According to The Angiogenesis Foundation, at least 184-million patients in Western nations alone could benefit from some form of anti-angiogenic therapy, and at least 314 million from some form of pro-angiogenic therapy. For example, anti-angiogenic therapy applies to all solid tumors (lung, breast, prostate, colon cancer etc.). The market for anti-angiogenic therapies is huge as implied by first quarter 2007 financial reports of Ranibizumab™, which treats age-related macular degeneration. It has already been a pharmaceutical blockbuster in 2007 with estimated annual revenues of over 1 billion dollars.

The mechanism of angiogenesis is not well understood; however, several factors have been identified to be involved in angiogenesis as angiogenesis stimulators and inhibitors. Some of the angiogenic factors are fibroblast growth factor, transforming growth factor-α, transforming growth factor-β, angiogenin, interleukin-8, platelet-derived growth factor, vascular endothelial growth factor (VEGF). Among them, VEGF is considered to be the most important cytokine in pathological angiogenesis.

Several potentially effective anti-angiogenic agents have been developed and investigated in animal, epidemiological and clinical studies (Kyselova et al., 2004). They could be classified as inhibitors of VEGF, antagonists of vascular endothelial growth factor receptors (VEGFRs), and VEGFR tyrosine kinase inhibitors. Inhibitors of VEGF could be humanized monoclonal antibodies of VEGF and VEGF trap—the soluble truncated form of VEGFR. VEGFRs antagonists could be humanized monoclonal antibodies or small-molecule inhibitors. Several small-molecule inhibitors of VEGFR tyrosine kinase inhibitors have been developed, of which some are selective to VEGFR2 and/or other VEGFRs and some less selectively target cancer growth. In addition, dopamine D2 receptor agonists were reported as anti-angiogenic agents with suggested mechanism of internalization of surface VEGFR-2 (Basu et al., 2001). The development of small molecule inhibitors of angiogenesis is regarded as an important therapeutic area as it offers potentially long-term treatment, with significantly fewer side effects than traditional chemotherapeutic treatment regimes.

Three specific inhibitors of VEGF are in the market: Bevacizumab™ (Genentech & Roche), Ranibizumab™ (Genentech & Novartis), and Pegaptanib™ (Pfizer). However, all of them are associated with high cost, thus the development of low cost anti-angiogenic drugs is highly desired.

We previously reported on the potent anti-glycation activity of catechols, dopamines and adrenalines (Yeboah et al., 2005), and its application to prevent cataract (Mullick & Konishi, 2007). Drug repositioning of adrenalines has advantages for topical ocular applications, as dipivefrin, a prodrug of (R,S)-adrenaline, is a commercial eye drop drug to treat glaucoma. Thus, we developed eye drops to prevent diabetic retinopathy based on adrenalines.

One of the lead compounds is (S)-isoproterenol. Systemic (S)-isoproterenol is 200 to 1600 times less effective than (R)-isoproterenol on blood pressure, rate of perfused heart, and uterine relaxation, demonstrating weak activity as β-adrenoceptor agonist (Lands et al., 1954). (S)-isoproterenol is an antagonist of α-adrenergic receptors as it shows antinociceptive action, where nociceptive action is typically caused by agonists of α2-adrenergic receptor (Bentley and Starr, 1986).

(S)-isoproterenol is considered to be safe for humans. The acute intravenous toxicity of (S)-isoproterenol in mice is approximately half of that of (R)-isoproterenol, i.e., $LD_{50}$ values of (S)-isoproterenol and (R)-isoproterenol were 113±5 mg/kg and 57±2 mg/kg, respectively (Lands, et al., 1954). Furthermore, (S)-isoproterenol is an inactive ingredient of commercial bronchodilator and topical anti-allergic drugs of (R,S)-isoproterenol. Some side effects of (S)-isoproterenol have been reported only at extremely high concentrations. Topically applied 10% (S)-isoproterenol in humans caused brief mild conjunctival hyperemia and irritation, and 20% (S)-isoproterenol eye drop produced marked conjunctival hyperemia and mild miosis that persisted for several hours (Kass at al., 1976). However, no systemic effects of heart rate, blood pressure, and hematologic or serum chemistry values as well as no change at necropsy were observed in rabbit even with 17.6% (S)-isoproterenol eye drop (Seidehamel et al., 1975). Also a large intravenous dose of (S)-isoproterenol appeared to have only slight and transient effects on blood pressure and pulse rate (Kass et al., 1976).

One of the prodrug forms of (S)-isoproterenol is (S)-isoproterenol dipivalate. Although no systemic study of (S)-isoproterenol dipivalate has been reported, the racemic mixture (R,S)-isoproterenol dipivalate (58 μg/kg) was intravenously injected in dogs. It produced the same responses as those of (R,S)-isoproterenol, i.e., large increase in heart rate and in cardiac output, marked decrease in total peripheral resistance, decrease in aortic pressure, in central venous pressure, and in left atrial pressure, and no significant change in pulmonary vascular resistance. These responses began slower and lasted longer than those of (R,S)-isoproterenol. The results suggest that (R,S)-isoproterenol dipivalate is inert and exerts the effects after it is hydrolyzed to (R,S)-isoproterenol (Wang, et al., 1977).

SUMMARY OF THE INVENTION

Surprisingly, it has now been found that (S)-isoform catecholamines and related compounds having S-configuration at β-carbon and having a lipophilicity greater than (S)-noradrenaline are anti-angiogenic. Moreover, it has also been found that catecholamines, whether (S)-isoform or (R)-isoform, in which a β-hydroxy group has been modified are also anti-angiogenic.

Thus, there is provided a use of an anti-angiogenic effective amount of a compound of formula (I)

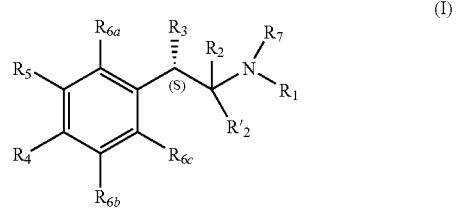

a physiologically tolerated salt thereof, a prodrug thereof, a physiologically functional derivative thereof or any mixture thereof as an anti-angiogenic agent, wherein: $R_1$ and $R_7$ each independently represents H, a $C_{1-10}$ alkyl group, a $C_{3-10}$ cycloalkyl group or a $C_{1-10}$ acyl group derived from an aliphatic acid or aromatic acid, or $R_1$ and $R_7$ are bonded together to form a $C_{3-7}$ nitrogen-containing heterocycle; $R_2$ and $R'_2$ each independently represents H, a $C_{1-10}$ alkyl group, a $C_{3-10}$ cycloalkyl group, or COOH, or one of $R_2$ or $R'_2$ is bonded together with $R_1$ to form a $C_{3-7}$ nitrogen-containing heterocycle; $R_3$ represents $OR_6$, $SR_8$, or $NR_8R_9$, wherein $R_8$ and $R_9$ each independently represents H, a $C_{1-10}$ alkyl group, a $C_{3-10}$ cycloalkyl group or a $C_{1-10}$ acyl group derived from an aliphatic acid or aromatic acid, provided that $R_8$ and $R_9$ are not both acyl groups; $R_4$ and $R_5$ each independently represents OY, NHY or SY, wherein Y represents H,

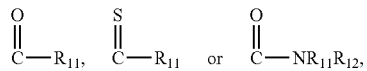

wherein $R_{11}$ and $R_{12}$ each independently represents H, a $C_{1-10}$ alkyl group or a $C_{3-10}$ cycloalkyl group; $R_{6a}$, $R_{6b}$ and $R_{6c}$ each represent independently H, F, Cl, Br, I, $OR_{10}$, or $SR_{10}$, wherein $R_{10}$ represents a $C_{1-10}$ acyl group derived from an aliphatic acid or aromatic acid; (S) represents a chiral centre defining an (S)-configuration of the compound; each $C_{1-10}$ alkyl group, $C_{3-10}$ cycloalkyl group, $C_{1-10}$ acyl group, $C_{3-8}$ nitrogen-containing heterocyclic group independently includes or does not include one or more heteroatoms N, O or S, and is independently unsubstituted or substituted with one or more $C_{6-10}$ aryl groups, $C_{6-18}$ alkaryl groups or $C_{6-18}$ aralkyl groups; and, provided that $R_1$ and $R_7$ are not both H when $R_2$ and $R'_2$ are both H. When Y does not represent H, Y is hydrolysable in vivo to give a compound where Y represents H.

There is further provided a use of an anti-angiogenic effective amount of a compound of formula (II)

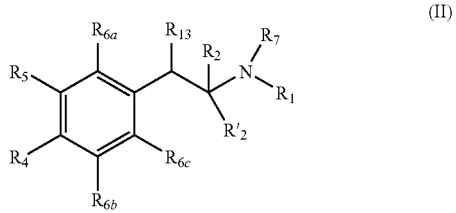

a physiologically tolerated salt thereof, a prodrug thereof, a physiologically functional derivative thereof or any mixture thereof as an anti-angiogenic agent, wherein: $R_1$ and $R_7$ each independently represents H, a $C_{1-10}$ alkyl group, a $C_{3-10}$ cycloalkyl group or a $C_{1-10}$ acyl group derived from an aliphatic acid or aromatic acid, or $R_1$ and $R_7$ are bonded together to form a $C_{3-7}$ nitrogen-containing heterocycle; $R_2$ and $R'_2$ each independently represents H, a $C_{1-10}$ alkyl group, a $C_{3-10}$ cycloalkyl group, or COON, or one of $R_2$ or $R'_2$ is bonded together with $R_1$ to form a $C_{3-7}$ nitrogen-containing heterocycle; $R_{13}$ represents $OR_{18}$, $SR_{18}$, or $NR_{18}R_{18}$, wherein $R_{15}$ and $R_{19}$ each independently represents a $C_{1-10}$ alkyl group, a $C_{3-10}$ cycloalkyl group or a $C_{1-10}$ acyl group derived from an aliphatic acid or aromatic acid, provided that $R_{18}$ and $R_{19}$ are not both acyl groups; $R_4$ and $R_5$ each independently represents OY, NHY or SY, wherein Y represents H,

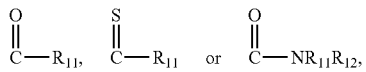

wherein $R_{11}$ and $R_{12}$ each independently represents H, a $C_{1-10}$ alkyl group or a $C_{3-10}$ cycloalkyl group; $R_{6a}$, $R_{6b}$ and $R_{6c}$ each represent independently H, F, Cl, Br, I, $OR_{10}$, or $SR_{10}$, wherein $R_{10}$ represents a $C_{1-10}$ acyl group derived from an aliphatic acid or aromatic acid; and, each $C_{1-10}$ alkyl group, $C_{3-10}$ cycloalkyl group, $C_{1-10}$ acyl group, $C_{3-8}$ nitrogen-containing heterocyclic group independently includes or does not include one or more heteroatoms N, O or S, and is independently unsubstituted or substituted with one or more $C_{6-10}$ aryl groups, $C_{6-18}$ alkaryl groups or $C_{6-18}$ aralkyl groups. When Y does not represent H, Y is hydrolysable in vivo to give a compound where Y represents H.

There is further provided a method for treating and/or preventing angiogenesis in a subject comprising administering to a subject an anti-angiogenic effective amount of an anti-angiogenic agent as described above.

There is further provided a use of an anti-angiogenic effective amount of the anti-angiogenic agent as described above for preparing a medicament for treating and/or preventing angiogenesis in a subject.

There is further provided a commercial package comprising an anti-angiogenic effective amount of the anti-angiogenic agent as described above together with instructions for use in treatment and/or prevention of angiogenesis in a subject.

$R_7$ preferably represents H. $R_1$ preferably represents a $C_{1-10}$ alkyl group. Preferably $R_2$ and $R'_2$ both represent H, or $R_2$ represents H and $R'_2$ represents —CH$_2$CH$_3$. $R_4$ and $R_5$ preferably each independently represents OY, and each Y preferably independently represents H, pivaloyl, acetyl, propionyl, butanoyl, isobutanoyl, pentanoyl, 2-butenoyl, cyclopropanoyl, cyclohexanoyl, benzoyl, 4-methylbenzoyl, 4-nitrobenzoyl, phenacetyl, 4-methylphenacetyl, methoxyacetyl, or N,N-dimethylamido. More preferably $R_4$ and $R_5$ each represent OY, and each Y represents H or pivaloyl. Y is most preferably H. Preferably, $R_{6a}$, $R_{6b}$ and $R_{6c}$ each represent H. In compounds of formula (I), $R_3$ preferably represents $OR_8$, and $R_8$ preferably represents a $C_{1-10}$ alkyl group. In compounds of formula (II), $R_{13}$ preferably represents $OR_{18}$ and $R_{18}$ preferably represents a $C_{1-10}$ alkyl group, more preferably —CH$_3$. Alkyl groups mentioned herein may be linear or branched.

For compounds of formula (I), the compound is preferably (S)-isoproterenol, (S)—N-ethylnoradrenaline, (S)—N-tert-butylnoradrenaline, (S)—N-n-butylnoradrenaline, (S)—N- n-propylnoradrenaline, 1-(3,4-dihydroxyphenyl)-2-(isopropylamino)-1(S)-butanol, erythro-(D,L)-dopaserine, dextronordefrin, (S)-dioxifedrine, (S)-dioxethedrin, (S)-norbudrine, (S)-4-(hydroxy-2-piperidinyl-methyl)-1,2-benzenediol, (S)-pipratecol, (S)-arbutamine, (S)-protokylol, (S)-theodrenalinel, (S,S')-hexoprenaline or (S)-PTFMA. More preferably, the compound is (S)-isoproterenol, (S)—N-ethylnoradrenaline, (S)—N-tert-butylnoradrenaline, (S)—N-n-butylnoradrenaline, (S)—N-n-propylnoradrenaline, 1-(3,4-dihydroxyphenyl)-2-(isopropylamino)-1(S)-butanol, erythro-(D,L)-dopaserine, dextronordefrin, (S)-dioxifedrine, (S)-dioxethedrin or (S)-norbudrine. Even more preferably, the compound is (S)-isoproterenol.

For anti-angiogenic agents based on compounds of formula (I), optical purity of the compound depends on the specific compound. Contamination of (R)-isomer must be low enough such that the anti-angiogenic activity of (S)-isomer exceeds any angiogenic activity of the corresponding (R)-isomer. Preferably, the anti-angiogenic agent has an optical purity of 50% w/w or greater, more preferably 95% or greater, even more preferably 97% or greater, yet even more preferably 99% or greater, still yet even more preferably 99.9% or greater, and yet still yet even more preferably 99.99% or greater. For topical applications, optical purity is preferably 97% w/w or greater, more preferably 99.9% or greater, while for systemic applications, optical purity is preferably 99.9% w/w or greater, more preferably 99.99% or greater. High purity both increases the anti-angiogenic effect of the anti-angiogenic agent and reduces possible β2-adrenergic receptor agonist effects of the (R)-isoform impurity in short and/or long-term uses. Further, β2-adrenergic receptor agonists are generally angiogenic (Thaker et al., 2006), which would be counterproductive to the anti-angiogenic effects of the (S)-isomer used in the present invention.

For compounds of formula (II), the compound is preferably 1-(N-isopropyl)-3-methoxydopamine, as the (S)-isoform, (R)-isoform or a mixture thereof.

Examples of physiologically tolerated salts include, but are not limited to, hydrochloride, bitartrate, acetate, carbonate, tannate, sulfate, stearate and citrate. Hydrochloride form is preferred.

Examples of prodrugs or physiologically functional derivatives include, but are not limited to, compounds comprising at least one $C_{1-10}$ acyl group derived from an aliphatic acid or aromatic acid. Acyl groups include, for example, pivaloyl, acetyl, propionyl, butanoyl, isobutanoyl, pentancyl, cyclopropanoyl, cyclohexanoyl, dibenzoyl and di(4-methylbenzoyl) groups (Jarvinen & Jarvinen, 1996). The pivaloyl (trimethylacetyl) group is a particularly preferred acyl group. Compounds bearing such acyl groups advantageously provide more efficient delivery of a therapeutically effective concentration of the compound to targeted tissues (e.g. to the retina for treating diabetic retinopathy), increase lipophilicity to effectively penetrate cell membranes, protect the compound from oxidative degradation, and protect the compound from racemization during storage.

The active anti-angiogenic agents may be formulated in pharmacologically acceptable compositions. In addition to the active anti-angiogenic agent in accordance with the present invention, the compositions may further comprise one or more pharmacologically tolerated ingredients, for example carriers (e.g. solvents), buffers, viscosity-adjusting agents, surfactants, anti-oxidants, preservatives, lubricants, osmolarity-adjusting agents, binders, glidants, anti-adherents, diluents, sweetening agents, colorants, flavorants, other pharmacologically active agents or mixtures thereof.

Compositions for the topical ocular administration according to the present invention may be formulated in any dosage form suitable for topical ophthalmic delivery, such as solutions, suspensions, or emulsions. Of those, aqueous ophthalmic solutions are preferred. Other than the anti-angiogenic agent, the compositions may further contain customary ophthalmic additives and excipients, such as antimicrobial preservative(s), viscosity-increasing agent(s) in order to increase the retention of the drugs and prodrugs, buffering agent(s), osmolarity-adjusting agent(s), surfactant(s), antioxidant(s) or mixtures thereof, if required or appropriate. The topical ocular treatment can be, but is not limited to, eye drop or intravitreous injection. It can also be applied by other methods such as soaking into soft contact lenses, which may reduce the effective concentration of the drugs or prodrugs with long duration.

Compositions for systemic administration according to the present invention may be, but not limited to, oral administration, inhalation, sublingual administration, intradermal injection, subcutaneous injection, intramuscular injection, intravenous injection, intraosseous infusions, or depot injections. In addition to the active anti-angiogenic agent, pharmacologically acceptable ingredients include, but are not limited to, dispersion media, binders, diluents, lubricants, anti-adherents, glidants, disintegrants, preservatives, flavors, antioxidants, sweeteners, colorants, flavorants or mixtures thereof.

In vitro anti-angiogenic activity is demonstrated at the concentration lower than about 100 µM, especially lower than about 50 µM, more especially lower than about 30 µM. A therapeutically effective dose to prevent/delay/treat angiogenesis, and cell invasion, is preferably about 0.01 to 10% w/v, especially preferably 0.01 to 5% w/v, particularly 0.01 to 1% w/v, and especially 0.1 to 0.5% w/v for topical application. The active anti-angiogenic agent can be formulated in unit dosage form. For example, in eye drop formulations, the unit dose is preferably 5-200 µL, more particularly 10-100 µL, especially 30-50 µL, wherein about 50 µL is a typical volume of each eye drop, i.e., 200 µL and 100 µL correspond to 4 and 2 eye drops in each dose. Some commercial eye drop products recommend 2 to 3 eye drops in each dose. For systemic treatment applications, the amount administered may be in a range of about 0.1 to 500 mg/kg/day, for example 1 to 200 mg/kg/day, particularly 50 to 100 mg/kg/day. The most effective dose for a particular regime is readily determined by those of skill in the art.

The use of an anti-angiogenic agent in accordance with the present invention permits treatment and/or prevention of a number of disease states, for example, diabetic retinopathy, diabetic macular edema, age-related macular degeneration, ischemic heart disorders, rheumatoid arthritis, psoriasis, tumorigenesis, metastasis and/or tumor growth. Mammalian subjects are preferred, for example, humans, rats, rabbits, dogs, cats, horses, cows, guinea pigs and mice.

Further features of the invention will be described or will become apparent in the course of the following detailed description.

BRIEF DESCRIPTION OF THE DRAWINGS

In order that the invention may be more clearly understood, embodiments thereof will now be described in detail by way of example, with reference to the accompanying drawings, in which.

DESCRIPTION OF PREFERRED EMBODIMENTS

Figure 1:
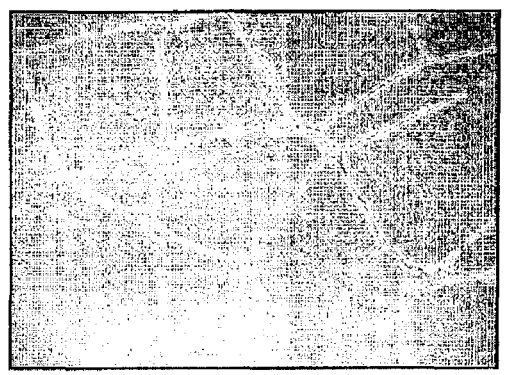
FIG. 1. Inhibition of in vitro capillary-tube formation of human umbilical vein endothelial cells (HUVECs) by (S)-isoproterenol. HUVECs were cultured in EBM-2 medium for 22 h at 37° C. on Matrigel in the presence of indicated concentrations (1-50 µM) of (S)-isoproterenol. The control represents the condition with no (S)-isoproterenol added to the medium.
Figure 1:
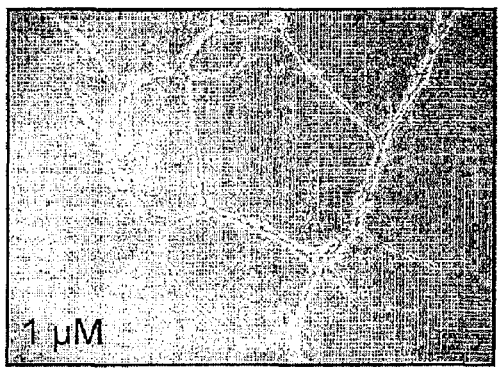
Figure 1:
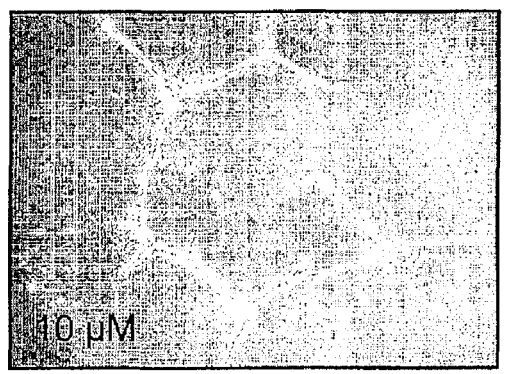
Figure 1:
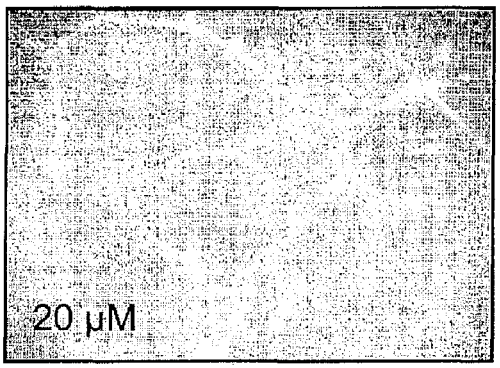
Figure 1:
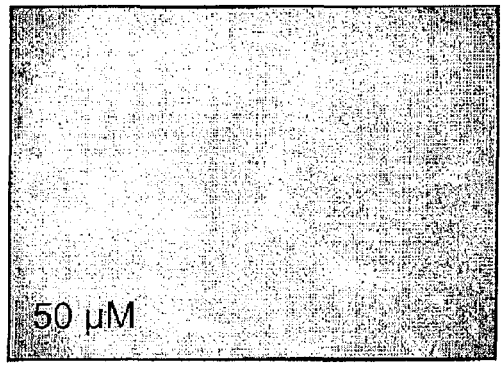

Materials and Methods:

Chemicals: (S)-isoproterenol L-bitartrate, (S)-noradrenaline L-bitartrate, D-mannitol, benzalkonium chloride, pivaloyl chloride (trimethylacetyl chloride), iodoethane, 1-iodopropane, 1-iodobutane, sodium borohydride, methyl trifluoromethanesulfonate, 2-chloro-3,4-dihydroxyacetophenone, 1,4-dioxane, p-toluoyl chloride, disodium sulfate, chlorobutanol, aminocaproic acid, sodium perchlorate, [Glu$^1$]-fibrinopeptide B, (R)-isoproterenol hydrochloride, isoetharine mesylate, di-tert-butyl dicarbonate, triethylamine, acetyl chloride, 2-propanol, dimethylformamide, tert-butylamine, isobutyryl chloride, benzoyl chloride, cetylpyridinium chloride and povidone (K30) were obtained from Sigma-Aldrich (Oakville, Ontario, Canada). Acetone, methylene chloride, ethyl acetate, glacial acetic acid, disodium carbonate, sodium chloride and NaOH were from EMD Science (Gibbstown, N.J., USA). Disodium edetate, trifluoroacetic acid (TFA), and water were purchased from J. T. Baker (Phillipsburg, N.J., USA). 1.0 M HCl was obtained from VWR (Montreal, Quebec, Canada). Water for mass spectrometry was purchased from Anachemia (Lachine, QC, Canada). Formic acid was purchased from Riedel de Haën (Oakville, Ontario, Canada). Acetonitrile and hexane were from Fisher Scientific (Nepean, Ontario, Canada). AG® 4-X4 resin, 100-200 mesh, free base form was purchased from BIO-RAD Laboratories, Inc (Hercules, Calif., USA). All the chemicals were used without further purification.

Cetylpyridinium trifluoroacetate was prepared from cetylpyridinium chloride. To a solution of sodium trifluoroacetate in methanol was added trifluoroacetic acid. The resulting methanolic solution of TFA-Na was then added dropwisely to the solution of cetylpyridinium chloride in ethanol with stirring. After 30 min, precipitated NaCl was filtered off and evaporated with rotary evaporator (<40° C.). The residue was dissolved in dichloromethane and insoluble components were filtered off. After evaporation, tert-butanol was added and lyophilized to obtain as a white crystal.

Cetylpyridinium acetate was prepared from cetylpyridinium chloride. Cetylpyridinium chloride was dissolved in methanol, and acetic acid and sodium acetate were added. After evaporating the solvent, the residue was dissolved in methylene chloride. Cetylpyridinium acetate was soluble in methylene chloride, whereas sodium chloride was precipitated and removed by filtration. The solvent was evaporated and the absence of chloride ion was confirmed as no precipitate was formed when silver nitrate solution was added to the product.

Synthesis of (S)-Noradrenaline Dipivalate Hydrochloride

This compound is used in the synthesis of (S)—N-ethylnoradrenaline hydrochloride, (S)—N-propylnoradrenaline hydrochloride, and (S)—N-butylnoradrenaline hydrochloride.

(S)—N-Boc-Noradrenaline

To a solution of (S)-noradrenaline bitartrate (3.83 g, 12 mmol) in 100 mL of tetrahydrofuran (THF)-water (1:1 v/v) was added sodium bicarbonate (3.3 g, 40 mmol), and stirred vigorously. Di-tert-butyl dicarbonate (2.9 g, 13.2 mmol) in THF (10 mL) was then added dropwise at room temperature. The reaction mixture was stirred for 3 hrs. The product (S)—N-Boc-noradrenaline was extracted with 50 mL of dichloromethane (DCM) three times. The combined extract was washed with water (50 mL) and brine (50 mL). The product solution was dried over sodium sulfate, filtered and then evaporated to dryness, yielding the desired product. The product showed over 95% purity based on the HPLC profile (an analytical Waters HPLC (Waters SymmetryShield™ 3.5 µm; 4.6×50 mm C18-reverse phase column). A gradient 10-90% acetonitrile in water, 0.1% trifluoroacetic acid (TFA), for 9 min at a flow rate of 2 mL/min (system A) was used. The product was further used without purification.

$C_{13}H_{19}NO_6$; white solid; Rt=4.9 min (system A). HRMS: calcd. for [M+H$^+$]=270.1341. found=270.1342. ESI-MS/MS (collision energy (CE)=2): m/z (% relative intensity): 270 (M+H$^+$, 94), 252 (100), 214 (1.3), 196 (51). NMR: 1H NMR (500 MHz, CD$_3$OD): δ 6.80 (s, 1H), 6.73 (d, J=8 Hz, 1H), 6.67 (d, J=7 Hz, 1H), 4.54 (dd(br), J=5, 7 Hz, 1H), 3.24 (dd, J=5, 13 Hz, 1H), 3.16 (dd, J=7, 14 Hz, 1H), 1.43 (s, 9H).

(S)—N-Boc-Noradrenaline Dipivalate

To a mixture of (S)—N-Boc-noradrenaline (3.0 g, 11 mmol) and triethylamine (5 mL, 36 mmol) in DCM (100 mL) was slowly added pivaloyl chloride (2.9 mL, 24 mmol) at 0° C. under nitrogen. The reaction mixture was stirred for 15 min at 0° C., and then for 2 hrs at room temperature. The product solution was washed with water (50 mL), dried over sodium sulfate and concentrated. Silica gel column chromatography (using a gradient of 20-40% ethyl acetate/hexane) afforded pure product (2.40 g, 46% yield from (S)-noradrenaline bitartrate) as a viscous liquid.

$C_{23}H_{35}NO_7$; viscous liquid; Rt=9.0 min (system A). HRMS: calcd. for [M+H$^+$]=438.2492. found=438.2482. ESI-MS/MS (CE=2): m/z (% relative intensity): 438 (M+H$^+$, 100), 420 (2.3), 382 (86). NMR: 1H NMR (500 MHz, CD$_3$OD): δ 7.29 (d, J=7 Hz, 1H), 7.17 (s, 1H), 7.14 (d, J=9 Hz, 1H), 4.74 (t(br), J=8 Hz, 1H), 3.28 (dd, 1H), 3.22 (dd, J=8, 15 Hz, 1H), 1.44 (s, 9H), 1.36 (s, 9H), 1.34 (s, 9H).

(S)-Noradrenaline Dipivalate Hydrochloride

To a solution of (S)—N-Boc-noradrenaline dipivalate (2.4 g, 5.5 mmol) in dry methanol (100 mL) was added dropwise acetyl chloride (8 mL, 110 mmol) at 0° C. The reaction mixture was stirred for 15 min at 0° C. and then at room temperature. The reaction was monitored by TLC. After completion of the reaction (3 hrs), the solvent was evaporated under reduced pressure and the product was purified by high performance displacement chromatography (HPDC) (0.1% TFA/water, 4 g/L of cetylpyridinium trifluoroacetate as eluent). The product was further used in the preparations of (S)—N-ethylnoradrenaline dipivalate hydrochloride, (S)—N-propyrnoradrenaline dipivalate hydrochloride, and (S)—N-butylnoradrenaline dipivalate hydrochloride as described below.

$C_{18}H_{28}NO_5Cl$; white solid; Rt=6.0 min (system A). HRMS: calcd. for [C18H27NO5+H$^+$]=338.1967. found=338.1983. ESI-MS/MS (CE=13): m/z (% relative intensity): 338 (M+H$^+$, 5.9), 320 (100), 236 (26). NMR: 1H NMR (500 MHz, CD$_3$OD): δ 7.36 (dd, J=2, 8 Hz, 1H), 7.27 (d, J=2 Hz, 1H), 7.20 (d, J=8 Hz, 1H), 4.94 (dd, J=4, 9 Hz, 1H), 3.20 (dd, J=4, 13 Hz, 1H), 3.04 (dd, J=9, 13 Hz, 1H), 1.36 (s, 9H), 1.35 (s, 9H).

Synthesis of (S)—N-Ethylnoradrenaline Hydrochloride (S)—N-Ethylnoradrenaline Dipivalate Hydrochloride (Prodrug)

To a solution of (S)-Noradrenaline dipivalate hydrochloride (0.37 g, 1.0 mmol) and triethylamine (0.4 mL, 3.0 mmol) in 10 mL of dry dimethylformamide (DMF) was added iodoethane (0.12 mL, 1.5 mmol). The reaction mixture was stirred for 24 hrs at room temperature under nitrogen and lyophilized. The mixture was taken up in ethyl acetate (30 mL) and extracted with NaH$_2$PO$_3$ buffer (4×20 mL, pH 3). The organic layer was extracted again with water (3×20 mL). Combined buffer extracts and water extracts were adjusted to pH 11 using 1.0 N NaOH and extracted with ethyl acetate (3×20 mL). The separated organic phase was further washed with water (20 mL) and brine (20 mL), dried over sodium sulfate and concentrated. Crude mixture was purified by HPDC (0.1% TFA/water, 4 g/L of cetylpyridinium trifluoroacetate as eluent). The isolated compound was treated with excess of 1.0 N HCl and lyophilized to give a solid mono-ethylation product (0.11 g, 27% yield).

$C_{20}H_{32}NO_5Cl$ (mono-ethylation); white solid; Rt=6.2 min (system A). HRMS: calcd. for [C$_{20}$H$_{31}$NO$_6$+H$^+$]=366.2280. found=366.2268. ESI-MS/MS (CE=15): m/z (% relative intensity): 366 (M+H$^+$, 55), 348 (100), 264 (24). NMR: 1H NMR (500 MHz, CD$_3$OD): δ 7.37 (dd, J=2, 8 Hz, 1H), 7.27 (d, J=2 Hz, 1H), 7.20 (d, J=8 Hz, 1H), 4.98 (dd, J=3, 10 Hz, 1H), 3.24 (dd, J=3, 13 Hz, 1H), 3.12 (m, 3H), 1.36 (s, 9H), 1.35 (s, 9H), 1.34 (t, J=7 Hz, 3H).

(S)—N-Ethylnoradrenaline Hydrochloride

To a solution of (S)—N-ethylnoradrenaline dipivalate hydrochloride (50 mg, 125 µmol) in dry methanol (3 mL) was added excess solid sodium borohydride and the reaction mixture was monitored by HPLC until no unreacted starting material remained. The solvent was evaporated to dryness giving white solid. Crude mixture was purified by preparative HPLC using 0.1% TFA/water as eluent. The residue was treated with excess 1.0 N HCl and lyophilized to give desired product as a white solid (22 mg, 76% yield).

$C_{10}H_{16}NO_3Cl$; white solid; Rt=0.53 min (system A). HRMS: calcd. for [C$_{10}$H$_{15}$NO$_3$+H$^+$]=198.1130. found=198.1128. ESI-MS/MS (CE=8): m/z (% relative intensity): 198 (M+H$^+$, 48), 180 (100). NMR: 1H NMR (500 MHz, DMSO-d6): δ 8.99 (s(br), 1H), 8.96 (s(br), 1H), 6.79 (s, 1H), 6.72 (d, J=8 Hz, 1H), 6.61 (d, J=9 Hz, 1H), 5.92 (s(br), 1H), 4.77 (d, J=10 Hz, 1H), 2.94 (m(br), 3H), 2.87 (t, J=12 Hz, 1H), 1.21 (t, J=7 Hz, 3H).

Synthesis of (S)—N-Propylnoradrenaline Hydrochloride

(S)—N-Propylnoradrenaline Dipivalate Hydrochloride (Prodrug)

To a mixture of (S)-noradrenaline dipivalate hydrochloride (0.37 g, 1.0 mmol) and triethylamine (0.4 mL, 3.0 mmol) in dry DMF (10 mL) was added iodopropane (0.15 mL, 1.5 mmol) and stirred for 24 hrs at room temperature under nitrogen. The resulting mixture was lyophilized. The mixture was taken up in ethyl acetate (30 mL) and extracted with $NaH_2PO_3$ buffer (4×20 mL, pH 3). The organic layer was extracted again with water (3×20 mL). Combined buffer extracts and water extracts were adjusted to pH 11 using 1.0 N NaOH and extracted with ethyl acetate (3×20 mL). The separated organic phase was further washed with water (20 mL) and brine (20 mL), dried over sodium sulfate and concentrated. Crude mixture was purified by HPDC (0.1% TFA/water, 4 g/L of cetylpyridinium trifluoroacetate as eluent). The isolated compound was treated with excess of 1.0 N HCl and lyophilized to give a solid product (0.09 g, 22% yield).

$C_{21}H_{34}NO_5Cl$; white solid; Rt=6.4 min (system A). HRMS: calcd. for $[C_{21}H_{33}NO_5+H^+]$=380.2437. found=380.2421. ESI-MS/MS (CE=15): m/z (% relative intensity): 380 (M+H$^+$, 78), 362 (100), 278 (20), 250 (0.9). NMR: 1H NMR (500 MHz, CD$_3$OD): δ 7.38 (d, J=8 Hz, 1H), 7.28 (s, 1H), 7.20 (d, J=8 Hz, 1H), 5.01 (dd, J=3, 10 Hz, 1H), 3.26 (d, J=13 Hz, 1H), 3.14 (t, J=10 Hz, 1H), 3.03 (t, J=8 Hz, 2H), 1.76 (m(br), 2H), 1.36 (s, 9H), 1.35 (s, 9H), 1.04 (t, J=7 Hz, 3H).

(S)—N-Propylnoradrenaline Hydrochloride

To a solution of (S)—N-propylnoradrenaline dipivalate hydrochloride (40 mg, 96 μmol) in dry methanol (3 mL) was added excess solid sodium borohydride and the reaction mixture was monitored by HPLC until no unreacted starting material remained. The solvent was evaporated to dryness giving white solid. Crude mixture was purified by preparative HPLC using 0.1% TFA/water as eluent. The residue was treated with excess 1.0 N HCl and lyophilized to give desired product as a white solid (15 mg, 63% yield).

$C_{11}H_{18}NO_3Cl$; white solid; Rt=0.57 min (system A). HRMS: calcd. for $[C_{11}H_{17}NO_3+H^+]$=212.1286. found=212.1280. ESI-MS/MS (CE=8): m/z (% relative intensity): 212 (M+H$^+$, 63), 194 (100). NMR: 1H NMR (500 MHz, DMSO-d6): δ 8.96 (s(br), 1H), 8.93 (s(br), 1H), 6.78 (s, 1H), 6.72 (d, J=8 Hz, 1H), 6.62 (d, J=9 Hz, 1H), 5.93 (d(br), J=3 Hz, 1H), 4.76 (d, J=9 Hz, 1H), 2.99 (m(br), 1H), 2.87 (m(br), 2H), 2.72 (m(br), 1H), 1.65 (m, 2H), 0.89 (m, 3H).

Synthesis of (S)—N-Butylnoradrenaline Hydrochloride

(S)—N-Butylnoradrenaline Dipivalate Hydrochloride (Prodrug)

To a mixture of (S)-noradrenaline dipivalate hydrochloride (0.56 g, 1.5 mmol) and triethylamine (0.6 mL, 4.5 mmol) in dry DMF (15 mL) was added iodobutane (0.26 mL, 2.25 mmol) and stirred at room temperature under nitrogen for 24 hrs. The resulting mixture was lyophilized. The mixture was taken up in ethyl acetate (40 mL) and extracted with $NaH_2PO_3$ buffer (4×20 mL, pH 3). The organic layer was extracted again with water (3×20 mL). Combined buffer extracts and water extracts were adjusted pH to 11 using 1.0 N NaOH and extracted with ethyl acetate (3×20 mL). The separated organic phase was further washed with water (20 mL) and brine (20 mL), dried over anhydrous sodium sulfate and concentrated. Crude mixture was purified by HPDC (0.1% TFA/water, 4 g/L of cetylpyridinium trifluoroacetate as eluent). The isolated compound was treated with excess of 1.0 N HCl and lyophilized to give a solid product (0.22 g, 34% yield).

$C_{22}H_{38}NO_5Cl$; white solid; Rt=6.7 min (system A). HRMS: calcd. for $[C_{22}H_{35}NO_6+H^+]$=394.2593. found=394.2582. ESI-MS/MS (CE=15): m/z (% relative intensity): 394 (M+H$^+$, 100), 376 (34), 292 (4). NMR: 1H NMR (500 MHz, CD$_3$OD): δ 7.37 (dd, J=2, 8 Hz, 1H), 7.28 (d, J=2 Hz, 1H), 7.21 (d, J=8 Hz, 1H), 5.00 (dd, J=3, 10 Hz, 1H), 3.25 (dd, J=3, 12 Hz, 1H), 3.14 (dd, J=10, 12 Hz, 1H), 3.06 (t, J=8 Hz, 2H), 1.71 (m(br), 2H), 1.46 (m, 2H), 1.36 (s, 9H), 1.35 (s, 9H), 1.01 (t, J=7 Hz, 3H).

(S)—N-Butylnoradrenaline Hydrochloride

To a solution of (S)—N-butylnoradrenaline dipivalate hydrochloride (50 mg, 120 μmol) in dry methanol (3 mL) was added excess solid sodium borohydride and the reaction mixture was monitored by HPLC until no unreacted starting material remained. The solvent was evaporated to dryness giving white solid. THF (10 mL) and saturated NaCl solution (10 mL) were added to the solid and extracted with THF (4×15 mL). Combined organic extracts were dried over anhydrous sodium sulfate, filtered, dried in vacuo. The residue was treated with excess 1.0 N HCl and lyophilized to give desired product as a white solid (25 mg, 80% yield).

$C_{12}H_{20}NO_3Cl$; white solid; Rt=0.84 min (system A). HRMS: calcd. for $[C_{12}H_{19}NO_3+H^+]$=226,1443. found=226.1437. ESI-MS/MS (CE=8): m/z (% relative intensity): 226 (M+H$^+$, 78), 208 (100). NMR: 1H NMR (500 MHz, DMSO-d6): δ 8.95 (s(br), 1H), 8.93 (s(br), 1H), 6.78 (d, J=2 Hz, 1H), 6.72 (d, J=9 Hz, 1H), 6.62 (dd, J=2, 9 Hz, 1H), 5.93 (d(br), J=3 Hz, 1H), 4.75 (d, J=9 Hz, 1H), 2.99 (dd, J=3, 13 Hz, 1H), 2.89 (m, 3H), 1.61 (m, 2H), 1.31 (m, 2H), 0.89 (t, J=8 Hz, 3H).

Synthesis of (R)—O-Methylisoproterenol Hydrochloride

To a solution of (R)-isoproterenol hydrochloride (123.6 mg, 0.5 mmol) in methanol (5 mL) was added methyl trifluoromethanesulfonate (220 μl, 2.0 mmol) at room temperature, and stirred overnight. After adding another methyl trifluoromethanesulfonate (220 μl, 2.0 mmol), the solution was stirred again overnight. The solvent was removed using evaporator. Then the residue was purified by preparative HPLC (Vydac C18, 5×25 cm column, isocratic solvent (0.1% TFA in 5% acetonitrile/water), flow rate 20 ml/min). The purified product was treated with 0.05 N HCl (10 mL), and lyophilized to give (R)—O-methylisoproterenol hydrochloride (62.3 mg 0.24 mmol, 48% yield) as a pale brown solid.

$C_{12}H_{20}NO_3Cl$; pale brown solid; Rt=4.6 min (system B). HRMS: calcd. for $[C_{12}H_{19}NO_3+H^+]$=226.1443. found=226.1440. ESI-MS/MS (CE=10): m/z (% relative intensity): 226 (M+H$^+$, 23), 194 (100). NMR: 1H NMR (500 MHz, CD$_3$OD): δ 6.79 (m, 2H), 6.69 (dd, J=3, 8 Hz, 1H), 4.34 (dd(br), J=3, 10 Hz, 1H), 3.40 (sept, J=6 Hz, 1H), 3.23 (s, 3H), 3.04-3.16 (m, 2H), 1.34 (d, J=6 Hz, 3H), 1.32 (d, J=6 Hz, 3H).

Synthesis of (S)—O-Methylisoproterenol Hydrochloride

To a solution of (S)-isoproterenol bitartrate (361 mg, 1.0 mmol) in methanol (1 mL), was slowly added methyl trifluoromethanesulfonate (1 mL, 8.0 mmol) at room temperature, and stirred for 4 hrs. The solvent was rapidly removed using evaporator and the product was then purified by preparative HPLC (Vydac C18, 5×25 cm column, gradient elution (0-40%, acetonitrile/water (0.1% TFA) with flow rate 20 mL/min). The purified compound was treated with 0.1 N HCl (10 mL) and lyophilized to give (S)—O-methylisoproterenol hydrochloride as a white solid. The product was analyzed by an analytical Waters HPLC (Waters SymmetryShield™ 3.5 μm; 4.6×50 mm C18-reverse phase column). A gradient 0-90% acetonitrile in water, 0.1% trifluoroacetic acid (TFA), for 12 min at a flow rate of 2 mL/min (system B) was used.

$C_{12}H_{20}NO_3Cl$; white solid; Rt=4.6 min (system B). HRMS: calcd. for $[C_{12}H_{19}NO_3+H^+]$=226.1443. found=226.1432. ESI-MS/MS (CE=10): m/z (% relative intensity): 226 (M+H$^+$, 17), 194 (100). NMR: 1H NMR (500 MHz, CD$_3$OD): δ 6.75 (m (br), 2H), 6.64 (d (br), J=6 Hz, 1H), 4.33 (d (br), J=8 Hz, 1H), 3.36 (m(br), 1H), 3.19 (s, 3H), 3.00-3.12 (m, 2H), 1.29 (t(br), J=7 Hz, 6H).

Synthesis of (R,S)—N-Tert-Butylnoradrenaline

ω-Tert-Butylamino-3,4-Dihydroxyacetophenone Hydrochloride

To a solution of ω-chloro-3,4-dihydroxyacetophenone (5 g, 26.8 mmol) in dioxane (10 mL), was added tert-butylamine (8.4 mL, 80 mmole), and stirred for 3 hrs at 70-80° C. The reaction was monitored by HPLC until no unreacted starting material remained. To the product amino ketone base was added 10% HCl. After cooling overnight at room temperature, the solid was filtered, washed with acetone, and dried to give amino ketone hydrochloride (5.62 g, 81% yield; m.p. 233-235° C.).

N-Tert-Butyl-Noradrenaline

To a stirred solution of ω-tert-butylamino-3,4-dihydroxyacetophenone hydrochloride (900 mg, 3.5 mmol) in methanol (20 mL), was slowly added NaBH$_4$ (266 mg, 7 mmol) at room temperature. The reaction was monitored by HPLC until no unreacted starting material remained (4 hrs). The solvent was evaporated and the product was further lyophilized, giving a crude free base (1.32 g). The crude free base (500 mg) was dissolved in 2.5 mL of water and adjusted to pH 9-10 with 10% HCl. After filtration, the resulting brown solution was eluted with 40% methanol/water on RP-18 column chromatography. The collected fractions were combined and dried in vacuo afforded a brown product, which was subjected to AG® 4-X4 Resin (100-200 mesh) column chromatography using pure water as eluent. After lyophilization, pure N-tert-butyl-noradrenaline was obtained as a yellowish crystal.

$C_{12}H_{19}NO_3$; yellowish crystal; Rt=4.5 min (system B). HRMS: calcd. for $[C_{12}H_{19}NO_3+H^+]$=226.1443. found=226.1432. ESI-MS/MS (CE=10): m/z (% relative intensity): 226 (M+H$^+$, 100), 208 (60), 152 (9). NMR: 1H NMR (500 MHz, CD$_3$OD): δ 6.63 (d, J=2 Hz, 1H), 6.50-6.60 (m, 2H), 4.66 (t, J=7 Hz, 1H), 3.00 (d, J=7 Hz, 2H), 1.33 (s, 9H).

Synthesis of (S)-Isoproterenol Diisobutyrate (Prodrug)

(S)—N-Boc-Isoproterenol

To a solution of (S)-isoproterenol bitartrate (1.0 g, 3 mmol) in DMF (15 mL), were added triethylamine (1.25 mL, 9 mmol) and Boc$_2$O (0.67 g, 3 mmol) at room temperature. The mixture was vigorously stirred overnight and the reaction was monitored by HPLC. The crude material was extracted with DCM (3×50 mL). The combined extract was washed with water (3×50 mL), and brine (50 mL) and dried over anhydrous sodium sulfate. The resulting residue was evaporated to dryness to obtain 0.96 g of pale brown solid. The product was used further without purification.

(S)—N-Boc-Isoproterenol Diisobutyrate

To a mixture of (S)—N-Boc-isoproterenol (0.96 g, 3 mmol) and triethylamine (0.98 mL, 7 mmol) in DCM (10 mL) was dropwisely added isobutyryl chloride (0.65 mL, 6 mmol) over 10 min at 0° C. under nitrogen and stirred for 2 hrs at room temperature. The crude material was extracted with DCM (3×50 mL), washed with water (3×50 mL) and brine (50 mL), and dried over anhydrous sodium sulfate. The resulting solution was evaporated to dryness to provide (S)—N-Boc-isoproterenol diisobutyrate as a white crystal (1.2 g), which was used further without purification.

(S)-Isoproterenol Diisobutyrate Hydrochloride

To a solution of (S)—N-Boc-isoproterenol diisobutyrate (1.2 g, 2.6 mmol) in isopropanol (10 mL) was added acetyl chloride (1.88 mL, 26 mmol) at 0° C. and stirred for 1.5 hrs at room temperature. The reaction was monitored by HPLC. After removing the solvent, the product (S)-isoproterenol diisobutyrate was purified by HPDC (0.1% TFA/water, 4 g/L of cetylpyridinium trifluoroacetate as eluent) to afford 319 mg (32% overall yield).

$C_{19}H_{30}NO_5Cl$:white solid:Rt=5.8 min (system A). HRMS: calc. for $[C_{19}H_{29}NO_5+H^+]$=352.2124. found=352.2119. NMR: 1H NMR (CD$_3$OD): δ 7.40 (d, J=8 Hz, 1H), 7.34 (brs, 1H), 7.24 (d, J=8 Hz, 1H), 5.02 (dd, J=3, 11 Hz, 1H), 3.47 (m, 1H), 3.25 (dd, J=3, 12 Hz, 1H), 3.13 (dd, J=10, 12 Hz, 1H), 2.83 (m, 2H), 1.37 (d, J=7 Hz, 6H), 1.30 (d, J=3 Hz, 12H).

Synthesis of (S)-Isoproterenol Dibenzoylate (Prodrug)

(S)—N-Boc-Isoproterenol

To a solution of (S)-isoproterenol bitartrate (1.0 g, 3 mmol) in DMF 15 mL, were added triethylamine (1.25 mL, 9 mmol) and Boc$_2$O (0.67 g, 3 mmol) at room temperature. The mixture was vigorously stirred overnight and the reaction was monitored by HPLC. The product was extracted with DCM (3×50 mL), washed with water (3×50 mL) and brine (50 mL), and dried over anhydrous sodium sulfate. The residue was further evaporated to dryness to obtain 0.85 g of pale brown solid. The product was used further without purification.

(S)—N-Boc-Isoproterenol Dibenzoylate

To a mixture of (S)—N-Boc-isoproterenol (0.85 g, 2.7 mmol) in DCM (10 mL) and triethylamine (0.89 mL, 6.4 mmol) was dropwisely added benzoyl chloride (0.63 mL, 5.4 mmol) over 10 min at 0° C. under nitrogen and stirred for 2 hrs at room temperature. The product was extracted with DCM (3×50 mL), washed with water (3×50 mL) and brine (50 mL), and dried over anhydrous sodium sulfate. The resulting solution was evaporated to dryness, providing (S)—N-Boc-isoproterenol dibenzoylate as a white crystal (1.43 g).

(S)-Isoproterenol Dibenzoylate

To a solution of (S)—N-Boc-isoproterenol dibenzoylate (1.43 g) in isopropanol (10 mL) was added acetyl chloride (2.01 mL, 28 mmol) at 0° C. and stirred for 1.5 hrs at room temperature. After removal the solvent, the desired (S)-isoproterenol dibenzoylate was purified by HPDC (0.1% TFA/H$_2$O, 4 g/L of cetylpyridinium trifluoroacetate as eluent) to yield 806 mg (64% overall yield).

C$_{25}$H$_{26}$NO$_5$Cl:white solid:Rt=6.3 min (system A). HRMS: calc. for [C$_{25}$H$_{25}$NO$_5$+H$^+$]=420.1811. found=420.1815. NMR: 1H NMR (CD$_3$OD): δ 8.03 (m, 4H), 7.63 (m, 2H), 7.60 (d, J=6.6 Hz, 1H), 7.49 (d, J=7.8 Hz, 1H), 7.49 (brs, 1H), 7.44 (m, 4H), 5.14 (dd, J=3, 10 Hz, 1H), 3.53 (m, 1H), 3.33 (dd, J=16.6 Hz, 1H), 3.21 (dd, J=10, 12 Hz, 1H), 1.41 (d, J=6.7 Hz, 6H).

Synthesis of (S)-Isoproterenol Ditoluoylate (Prodrug)

(S)—N-Boc-Isoproterenol

To a solution of (S)-isoproterenol bitartrate (1.0 g, 3 mmol) in DMF 15 mL, were added triethylamine (1.25 mL, 9 mmol) and Boc$_2$O (0.67 g, 3 mmol) at room temperature. The mixture was vigorously stirred overnight, and the reaction was monitored by HPLC. (S)—N-Boc-isoproterenol was extracted with DCM (3×50 mL), washed with water (3×50 mL) and brine (50 mL), and dried over anhydrous sodium sulfate. The solvent was evaporated to dryness to obtain 0.91 g of pale brown solid.

(S)—N-Boc-Isoproterenol Ditoluoylate

To a mixture of (S)—N-Boc-isoproterenol (0.91 g, 2.9 mmol) in DCM (10 mL) and triethylamine (0.94 mL, 6.8 mmol) was dropwisely added toluoyl chloride (0.77 mL, 5.4 mmol) over 10 min at 0° C. under nitrogen and stirred for 2 hrs at room temperature. The product was extracted with DCM (3×50 mL), washed with water (3×50 mL) and brine (50 mL), and dried over anhydrous sodium sulfate. The solution was evaporated to dryness to provide (S)—N-Boc-isoproterenol ditoluoylate as a white crystal (1.52 g).

(S)-Isoproterenol Ditoluoylate

To a solution of (S)—N-Boc-isoproterenol ditoluoylate (1.52 g) in isopropanol (10 mL) was added acetyl chloride (2.04 mL, 28 mmol) at 0° C. and stirred for 1.5 hrs at room temperature. After removal the solvent, the desired (S)-isoproterenol ditoluoylate was purified by HPDC (0.1% TFA/H$_2$O, 4 g/L of cetylpyridinium trifluoroacetate as eluent) to afford 715 mg (55% overall yield).

C$_{27}$H$_{30}$NO$_5$Cl:white solid:Rt=6.8 min (system A). HRMS: calc. for [C$_{27}$H$_{29}$NO$_5$+H$^+$]=448.2124. found=448.2109. NMR: 1H NMR (CD$_3$OD): δ 7.89 (d, Hz, 4H), 7.53 (d, J=8 Hz, 1H), 7.50 (d, J=8 Hz, 1H), 7.45 (brs, 1H), 7.24 (d, J=7 Hz, 4H), 5.06 (dd, J=3, 10 Hz, 1H), 3.49 (m, 1H), 3.31 (dd, J=10 Hz, 1H), 3.19 (dd, J=10, 13 Hz, 1H), 2.38 (s, 6H), 1.38 (d, J=7 Hz, 6H).

Synthesis of Isoetharine Dipivalate Hydrochloride (Prodrug)

To a solution of isoetharine mesylate (1.68 g, 5 mmol) in acetone (25 mL) was added 1.0 N NaOH (25 mL, 25 mmol) at room temperature and stirred for 10 sec, followed by addition of pivaloyl chloride (2.47 mL, 20 mmol) in one portion. The reaction solution was stirred for additional 15 sec. and then quenched with 1.0 N HCl (20 mL). The product was extracted with DCM (3×100 mL), washed with 10% sodium bicarbonate (100 mL) and brine (50 mL), dried over anhydrous sodium sulfate, filtered and concentrated in vacuo. Crude product was purified by HPDC (0.1% TFA/water, 4 g/L of cetylpyridinium trifluoroacetate as eluent) yielding white solid (1.0 g, 45% yield).

C$_{23}$H$_{38}$NO$_5$Cl; white solid; Rt=6.6 min (system A). HRMS: calcd. for [C$_{23}$H$_{37}$NO$_5$+H$^+$]=408.2750. found=408.2732. ESI-MS/MS (CE=15): m/z (% relative intensity): 408 (M+H$^+$, 100), 390 (16), 348 (0.8), 306 (2.3). NMR: 1H NMR (500 MHz, CD$_3$OD): δ 7.39 (dd, J=2, 9 Hz, 1H), 7.32 (d, J=2 Hz, 1H), 7.21 (d, J=9 Hz, 1H), 5.17 (d, J=4 Hz, 1H), 3.60 (sept, J=6 Hz, 1H), 3.42 (m, 1H), 1.69 (m, 1H), 1.59 (m, 1H), 1.44 (s, 3H), 1.43 (s, 3H), 1.36 (s, 9H), 1.35 (s, 9H), 0.87 (t, J=7 Hz, 3H).

The purity of (S)-isoproterenol dipivalate hydrochloride was examined by Waters analytical HPLC system (600-MS controller, 600E pump, 717 autosampler, 996 photodiode array detector). The optical purity of (S)-isoproterenol bitartrate and (S)-isoproterenol dipivalate hydrochloride was examined by using another Waters HPLC system (600 controller, 600E pump, 717 autosampler, an d2996 photodiode array detector). High performance displacement chromatography (HPDC) was also carried out by using the latter system. NMR spectra were measured by Bruker Avance 500 MHz NMR. High-resolution mass spectra were measured by MicroMass Waters Q-T of Ultima™ GLOBAL mass spectrometer (Mississauga, Ont, Canada) with NanoLockspray ([Glu$^1$]-fibrinopeptide B as a reference compound).

HUVECs were purchased from Cedarlane Laboratories (Burlington, Canada) and maintained in Endothelial Cell Basal Medium-2 (EBM-2) supplemented with EGM-2 growth factor mixture (Clonetics) and 2% Foetal bovine serum. The cells were cultured at 37° C. under a humidified 95%/5% (v/v) mixture of air and CO$_2$.

Matrigel endothelial cell tube formation assays were performed using BD Matrigel™ (Becton, Dickinson). BD Matrigel™ was thawed at 4° C., and 150 µL were quickly added to each well of a 48-well plate and allowed to solidify for 60 min at 37° C. HUVECs (7×10$^4$ cells/mL) In EC basal medium-2 (EBM-2) were seeded 250 µL per well onto the surface of the solid BD Matrigel™ in the presence of the compounds to be tested. The cells were incubated for 22 h at 3° C. in a 5% CO$_2$ incubator. Tube formation was monitored by using a Leitz Labovert (Leitz, Wetzlar, Germany) inverted microscope. Two randomly selected two microscopic fields were photographed with a digital camera (Nikon, COOLPICKS 995). The total length of tube structures in each photograph was measured using ImageJ™ free software (http://rsb.info.nih.gov/ij/) and was normalized to that of control with no test compound. Each reported value represents the average of total six photographs from three independent experiments.

Invasion of endothelial cells was measured using BD BioCoat™ Growth Factor Reduced Matrigel™ Invasion Chambers (Beckton-Dickinson; 8 mm pore size). EBM-2 medium (500 µL each) was placed into the lower wells. HUVECs (2.5×10$^4$) in EBM-2 serum-free medium (500 µL) were seeded into each of the upper wells and incubated in the presence of a test compound. HUVECs were allowed to migrate for 36 h at 37° C. in an atmosphere of 95% air/5% CO$_2$. HUVECs that remained on the upper surface of the filter were removed using a cotton swab. HUVECs that had migrated to the lower surface of the filters were fixed with methanol, stained with 0.1% crystal violet/20% (v/v) methanol and examined using a Leitz Labovert (Leitz, Wetzlar, Germany) inverted microscope after mounting on a slide. Three randomly selected microscopic fields were digitally captured using a Nikon COOLPICKS™ 995 digital camera and the number of HUVECs in each photograph were directly counted. Each reported value represents the average and standard deviation of a total four photographs from two independent experiments.

(S)-isoproterenol dipivalate hydrochloride used in the animal study was synthesized from (S)-isoproterenol bitartrate. Pivaloyl chloride (trimethylacetyl chloride) (4.1 mmol, 500 mL) was added to a solution of (S)-isoproterenol bitartrate (1.0 mmol, 361.3 mg) in 50% 1.0 N NaOH aq/acetone (5.5 ml/5.5 mL). The mixture was allowed to react at room temperature for 1 h. The solution was acidified to pH 3-5 using 1.0 N HCl. After washing with n-hexane (Fisher; Nepean, Ontario, Canada), the solution was extracted with DCM. The organic layer was washed with 10% $Na_2CO_3$ aqueous solution, dried over anhydrous sodium sulfate, and concentrated under reduced pressure. The residue was purified by high performance displacement chromatography (column; Shiseido Capcell™ PAK C18 AQ 5 μm; 250×4.6 mm; 4.0 mg/mL cetylpyridinium acetate 0.1% acetic acid in water, flow rate; 1.0 mL/min). The product was eluted out by a displacer, 4.0 mg/ml cetylpyridinium acetate 0.1% acetic acid in water. After salt exchange using 0.1 N HCl and lyophilization, (S)-isoproterenol dipivalate hydrochloride was obtained in 32±4% yield and 97.2±0.7% purity based on quantification of impurities described below.

$C_{21}H_{34}NO_5Cl$; white solid; Rt=6.6 min (system A). HRMS: calcd. for $[C_{21}H_{33}NO_5+H^+]$=380.2437. found=380.2426. 1H NMR (500 MHz, $CD_3OD$) δ 7.33 (dd, 7.2, 1.9 Hz, 1H), 7.24 (d, 1.9 Hz, 1H), 7.15 (d, 7.2 Hz, 1H), 4.96 (dd, 9.9, 3.1 Hz, 1H), 3.40 (m, 1H), 3.18 (dd, 12.3, 3.1 Hz, 1H), 3.07 (dd, 12.62, 9.9 Hz, 1H), 1.32 (d, 7.0 Hz, 6H), 1.30 (s, 9H), 1.29 (s, 9H).

The optical isomers of (S)-isoproterenol bitartrate and (S)-isoproterenol dipivalate hydrochloride were separated by HPLC using Shiseido chiral CD-Ph column (250×4.6 mm; 5 μm; isocratic 60:40 of 0.5 M sodium perchlorate/water and acetonitrile; flow rate, 1.0 mL/min). The elution profile was monitored by the absorption at 223 nm for isoproterenol bitartrate and 264 nm for isoproterenol dipivalate hydrochloride. The optical impurities were quantitated by the absorbance at 223 nm for isoproterenol bitartrate and 264 nm for isoproterenol dipivalate hydrochloride and by using a curve fitting software TABLECurve2D (Systat). The impurities of (R)-isoproterenol bitartrate and (R)-isoproterenol dipivalate hydrochloride were estimated as 2.0±0.3% and 3.3±0.2%, respectively. Thus, the racemization induced during synthesis and purification was minimal, if it occurred.

(S)-isoproterenol hydrochloride and (S)-isoproterenol dipivalate hydrochloride used in in vitro studies have 99.9% or higher optical purity.

In Vivo Studies:

(S)-isoproterenol dipivalate hydrochloride was used to study diabetic retinopathy in a rat model. Another advantage of adrenalines is the formulation, i.e., commercial eye drop dipivefrin is a prodrug of (R,S)-adremaline. It is more lipophilic than adrenaline, is still water soluble and stable in eye drop solution. Adrenaline is release when it passes through cornea, and pivalic acid, cleaved form of the blocking group, has a wide margin of safety, even at large oral administration. Dipivefrin enhances the ocular absorption 17 time better than adrenaline, allowing one to reduce the amount of the dose and the potential side effects (Mandell et al., 1978). The same formulation of prodrug was successfully applied to isoproterenol (Hussain & Truelove, 1975). Thus, the effect of the formulated (S)-isoproterenol dipivalate hydrochloride on diabetic retinopathy with rat model was examined.

Active ingredient in the eye drop is 0.10% (w/v) (S)-isoproterenol dipivalate hydrochloride, and inactive ingredients are 1.84% (m/v) D-mannitol, 0.005% (w/v) disodium edetate, 0.10% (w/v) chlorobutanol, 0.16% (w/v) ε-aminocaproic add, 0.5% (w/v) sodium chloride, 0.003% (w/v) benzalkonium chloride, and 0.20% (w/v) povidone. The pH of the eye drop was adjusted to 5.5 with 1.0 N HCl. The control eye drop has the same inactive ingredients, but lacks the active ingredient. The eye drop was freshly prepared every month and was stored at 4° C. No degradation of the active and inactive gradients was detected based on their HPLC profiles after one month of storage at 4° C. The volume of each eye drop was 50 μL.

Prevention of diabetic retinopathy by (S)-isoproterenol dipivalate eye drop was studied using a rat model. Two-month-old male Sprague-Dawley rats were purchased from Charles River, Canada. They were housed in the Biotechnology Research Institute (BRI)-animal facility. Housing and all experimental manipulations were approved by the BRI Animal Care Committee that functions under the guidelines of the Canadian Council of Animal Care. Diabetes was induced in male Sprague-Dawley rats weighing approximately 200 to 250 g by a single intraperitoneal injection of the beta-cell toxin, Streptozotocin (STZ) (Sigma, St. Louis, Mich.), at a dose of 60 mg/kg body weight in 0.1M citrate buffer pH 4.5. Non-diabetic control rats received citrate buffer only.

One week following induction of diabetes, glucose levels were determined in the blood sampled from the tail vein using a blood glucose monitoring system (Ascensia ELITE Blood Glucose Meter, Bayer Inc, Toronto, ON, Canada). Since the limit of detection of the blood glucose meter was 33 mM, any value above that has been assigned a maximum value of 35 mM. Only animals with blood glucose levels higher than 15 mM were retained in the study. Animals were thus allocated into one of four groups: Group I (n~20): Non-diabetic rats-receiving vehicle; Group II (n~20): Non-diabetic rats receiving eye drops containing (S)-isoproterenol dipivalate; Group III (n~20): Diabetic rats-receiving vehicle; Group IV (n~20): Diabetic rats-receiving eye drops containing (S)-isoproterenol dipivalate.

Eye drops or vehicle were administered twice a day, seven days a week, on the cornea of different groups of rats, with a minimum interval of 7 h between the two treatments. To promote weight gain and limit hyperglycemia, diabetic rats were injected sub-cutaneously with 2 IU ultralente insulin (Humulin, Eli Lilly, Toronto, ON, Canada) three times a week. Animal weights were monitored every week.

The effects of (S)-isoproterenol on diabetic retinopathy were studied by staining retinal capillaries with antibodies against lectin. The capillary density at the retinal center, corresponding to the macular of the human eye, was analyzed.

Diabetes induces glycation in retina. Since (S)-isoproterenol is a potent anti-glycation agent, penetration of (S)-isoproterenol reduces glycation in diabetic retinal capillaries. Thus, the retinas, which were stained with antibodies against lectin, were also stained with antibodies against glycated bovine serum albumin, and the degree of glycation of retinal capillaries was analyzed.

Results:

Anti-angiogenic activity of catecholamines and related compounds was measured by inhibiting capillary tube formation of (HUVECs in Matrigel assay (FIG. 1). The potency of (S)-isoproterenol is around 10 μM under the angiogenic assay condition used in FIG. 1. As dopamine showed comparable potency in the same assay (FIG. 2A) and showed effective anti-angiogenic activity at 1 μM (Basu et al., 2001), the in vivo potency of (S)-isoproterenol could be lower than 10 μM.

Figure 2A:
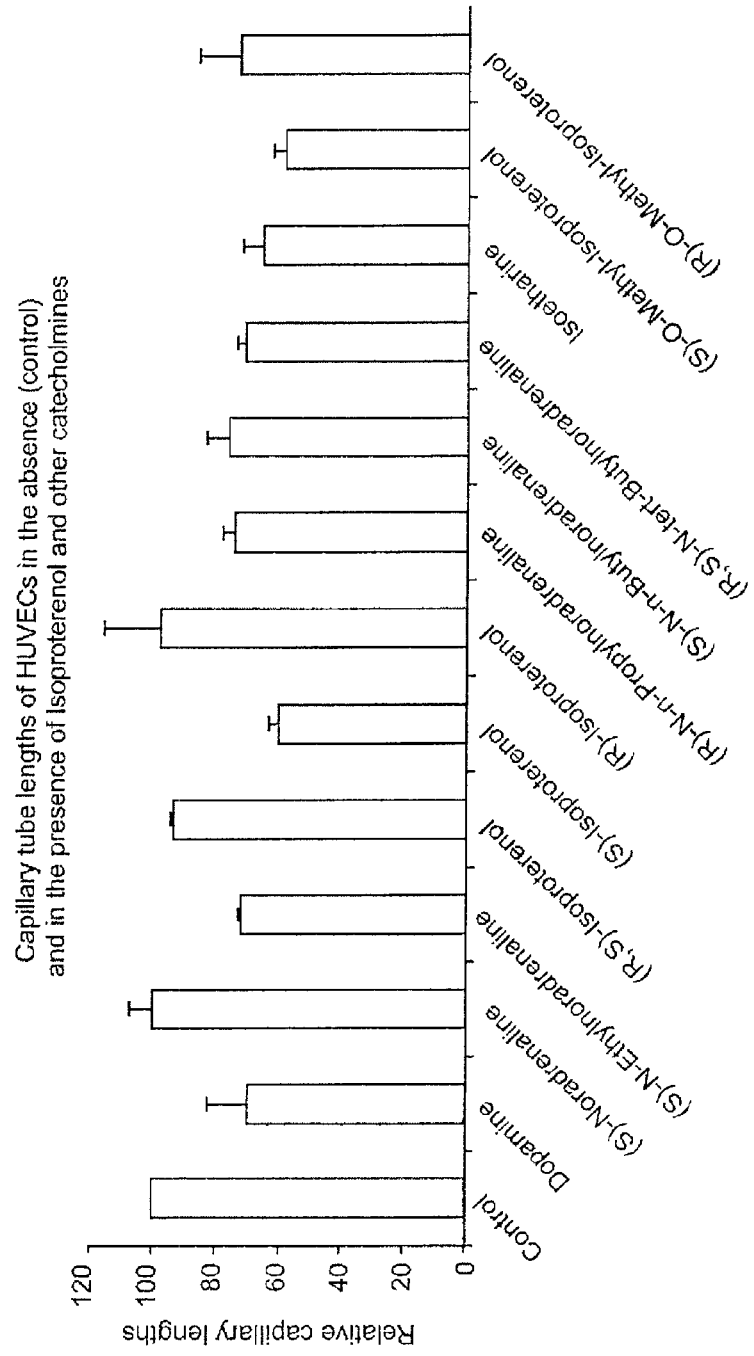
FIG. 2. Anti-angiogenic activity of (S)-isoproterenol and its analogs was measured by in vitro Matrigel endothelial cell capillary-tube formation assay. HUVECs were cultured on Matrigel™ in the absence (control) and in the presence of dopamine, (S)-noradrenaline, (S)—N-ethylnoradrenaline, (R,S)-isoproterenol, (S)-isoproterenol, (R)-isoproterenol, (S)—N-propylnoradrenaline, (S)—N-n-butylnoradrenaline, (R,S)—N-tert-butylnoradrenaline, isoetharine, (S)—O-methylisoproterenol, and (R)—O-methylisoproterenol of which concentrations were adjusted to 20 µM. After 22 h of incubation, two randomly selected microscopic fields were photographed for each cell culture. The total length of tube structures of HUVECs in each photograph was measured using ImageJ™ free software and normalized with that of control culture. The data of total six photographs from three independent experiments were averaged with standard deviation. (A) The data of total six photographs from three independent experiments were averaged with standard deviation. (B) Some of the photographs used in the analysis are shown.
Figure 2B:
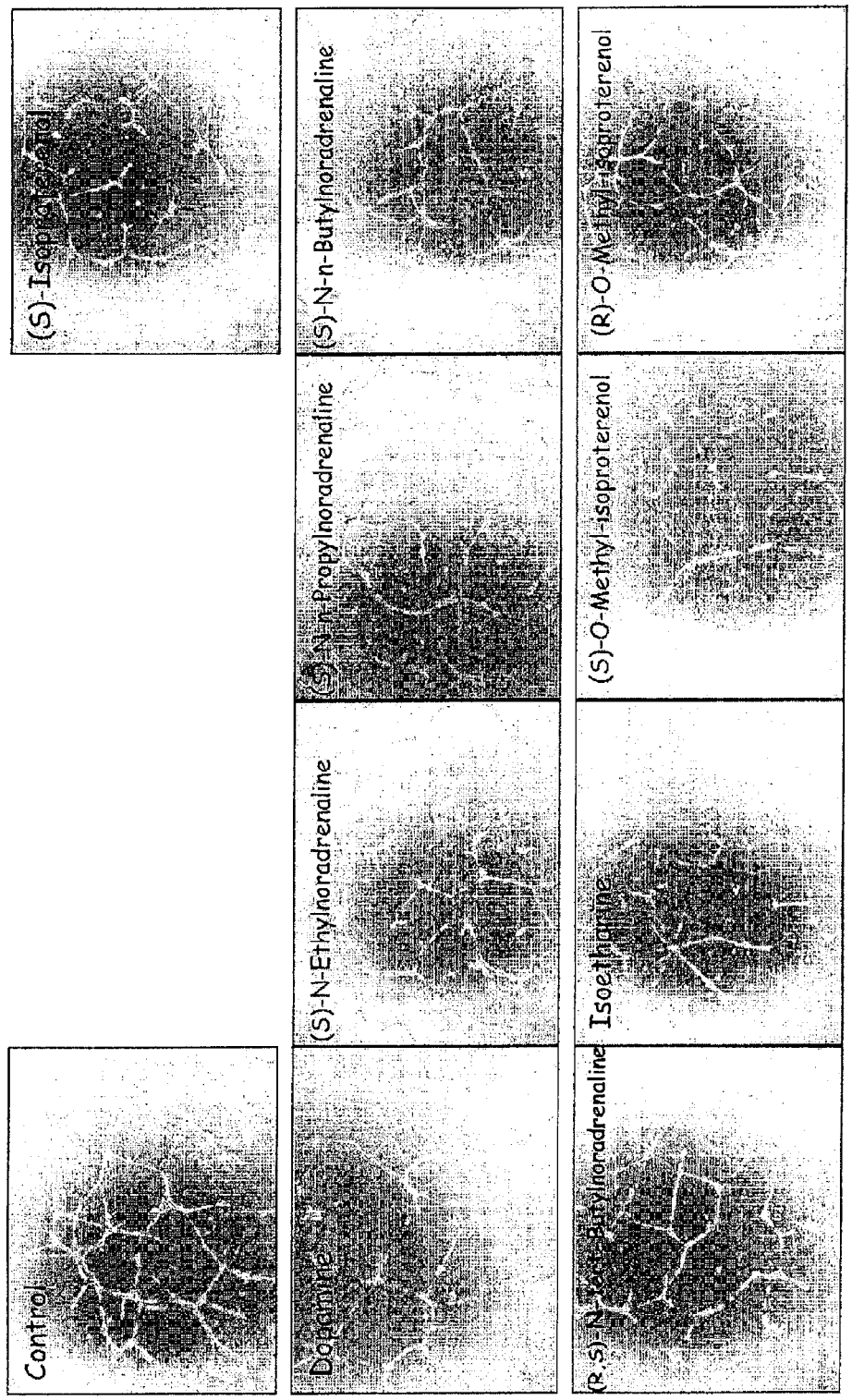

The anti-angiogenicity of some anti-angiogenic agents of the present invention is listed in Table 1A. Table 1B lists dopamine, a known anti-angiogenic compound, and some catecholamines that do not show anti-angiogenic effects. FIG. 2A is the quantitative expression of the anti-angiogenicity of these compounds and FIG. 2B are some of the photographs used in the analysis.

Dopamine is an anti-angiogenic agent through dopamine D2 receptor (Basu et al., 2001), whereas (R)-adrenalines (belonging to the catecholamine class of compounds) are angiogenic through β2-adrenergic receptor (Thake et al., 2006). It was surprising and unexpected that (S)-noradrenaline, which is structurally homologous to dopamine, was not anti-angiogenic, whereas (S)-isoproterenol, which is less homologous to dopamine than (S)-noradrenaline, was anti-angiogenic. Moreover, even less homologous (R,S)—N-tert-butylnoradrenaline was anti-angiogenic, despite (R)—N-tert-butylnoradrenaline being an agonist of β2-adrenergic receptor (Walker et al., 1985). Consequently, anti-angiogenic activity of the compounds listed in Table 1A is unexpected.

Figure 3:
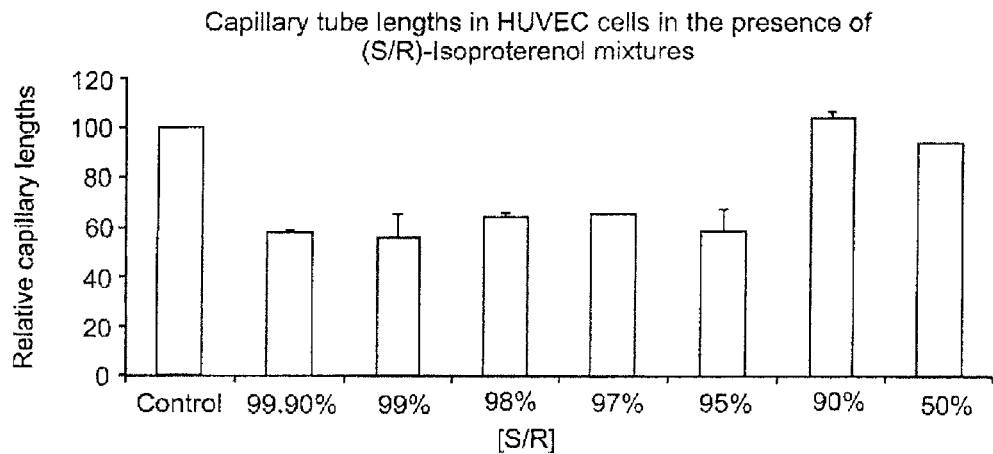
FIG. 3. Competition of (S)-isoproterenol with (R)-isoproterenol in in vitro capillary-tube formation. HUVECs were cultured on Matrigel™ in the presence of various ratios of (S)-isoproterenol and (R)-isoproterenol, where total concentration of isoproterenol was maintained to 20 µM. After 22 h of incubation, two randomly selected microscopic fields were photographed for each cell culture. The total length of tube structures in each photograph was measured using ImageJ™ free software and normalized with that of control culture, which contains no isoproterenol. The data of total six photographs from three independent experiments were averaged with standard deviation.
Figure 4:
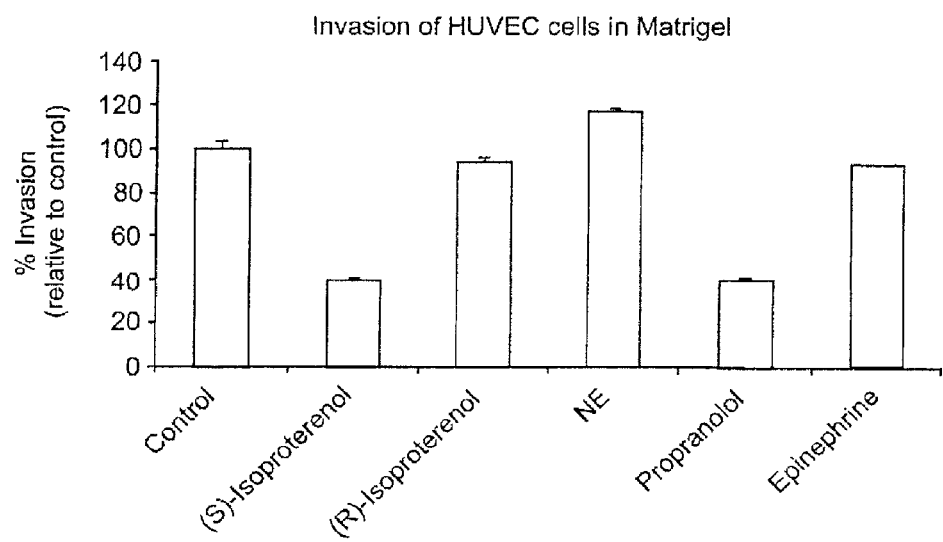
FIG. 4. Anti-invasion activity of (S)-isoproterenol and its analogs as well as β-adrenergic receptor antagonist propranolol was measured by HUVECs invasion through a Matrigel-coated filter and was normalized with the value of control HUVECs with no test compound added. The values are the average and standard deviation of a total of four photographs from two independent experiments.

(R)-Isoproterenol is known to be angiogenic and competes with the anti-angiogenic activity of (S)-isoproterenol as racemic mixture (R,S)-isoproterenol did not show anti-angiogenic activity. Thus, the optical purity of (S)-isoproterenol required to express anti-angiogenic activity was examined with various optical purity of (S)-isoproterenol (FIG. 3). Anti-angiogenic activity was observed with 97% w/w or higher optical purity of (S)-isoproterenol, while 95% w/w optically pure (S)-isoproterenol was in the transition from non-antianglogenic to anti-angiogenic. Consequently, at least 97% w/w optically purity of (S)-isoproterenol is preferred, more preferably at least 99.9% w/w, even more preferably at least 99.99% w/w, because the in vivo expression of β2-adrenergic receptor in the targeted tissue could be higher than that in HUVECs used in the assay, requiring further elimination of (R)-isoproterenol in the drug.

Figure 7:
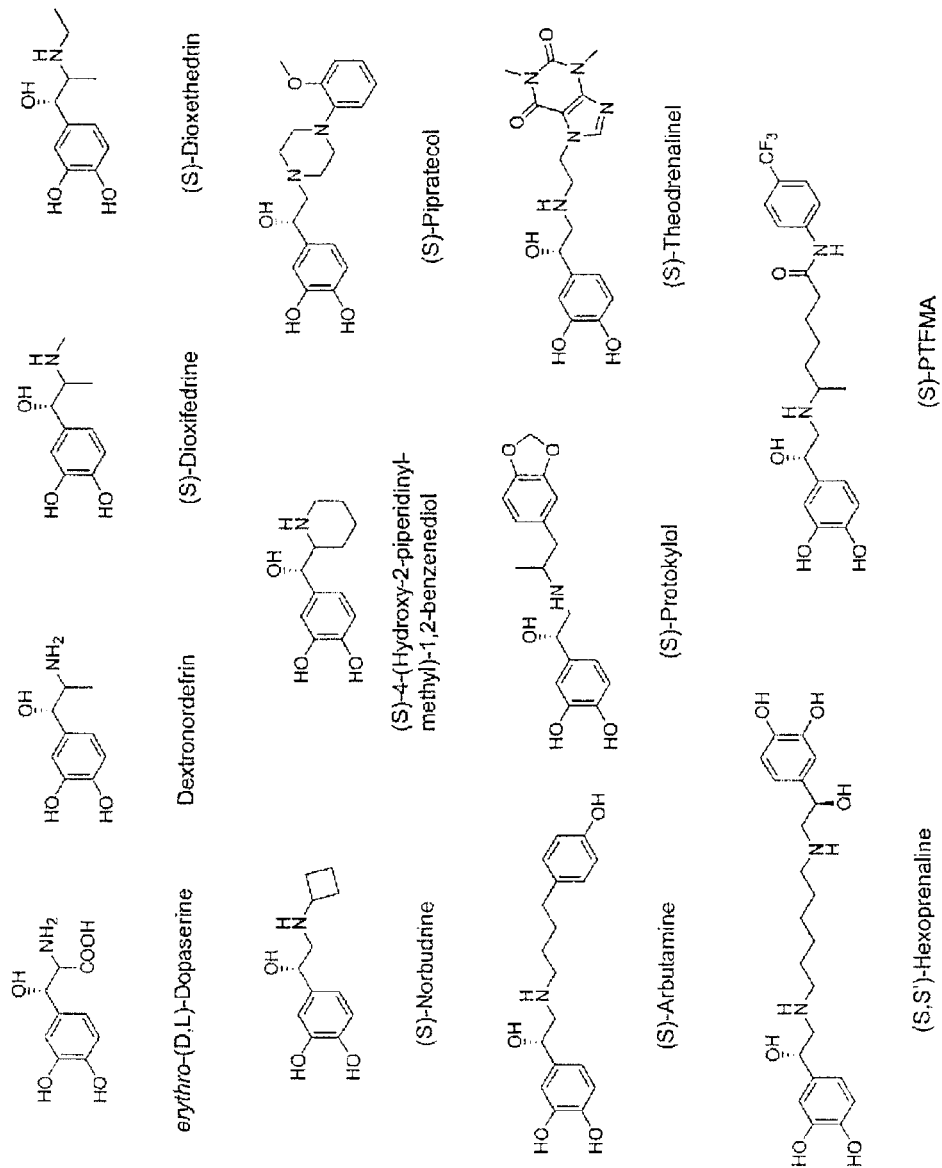
FIG. 7. Chemical structures of some compounds useful in the present invention.

Some (S)-adrenalines listed in Tables 1A and 1B are (S)-noradrenaline, (R,S)-adrenaline, (S)—N-ethylnoradrenaline, (S)—N-propylnoradrenaline, (S)—N-butylnoradrenaline, (R,S)—N-tert-butylnoradrenaline (Colterol), and isoetharine. The least lipophilic (S)-noradrenaline was not anti-angiogenic, whereas more lipophilic (S)—N-ethylnoradrenaline, (S)—N-propylnoradrenaline, (S)-isoproterenol, (S)—N-butylnoradrenaline showed anti-angiogenic activity. In racemic mixture, relatively lipophilic (R,S)-adrenaline and (R,S)-isoproterenol showed no anti-angiogenic activity. However, more lipophilic (R,S)—N-tert-butylnoradrenaline and isoetharine showed anti-angiogenic activity. Since (R)-isoform of these adrenalines is angiogenic through their β2-adrenergic receptor agonist activity, anti-angiogenic activity of (S)-isoform of these adrenalines might be enhanced as their lipophilicity is increased. Examples of some other (S)-adrenalines useful in the present invention are listed in FIG. 7.

TABLE 1A

Anti-angiogenicity of compounds of present invention.

| Compound (measured at 20 μM) | Structure | Activity |
|---|---|---|
| (S)-isoproterenol (>99.9% optically pure) | 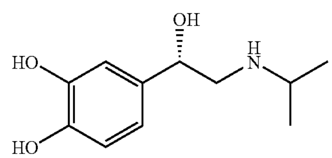 | Anti-angiogenic; Anti-invasive |
| (S)-N-ethylnoradrenaline (>99% optically pure) | 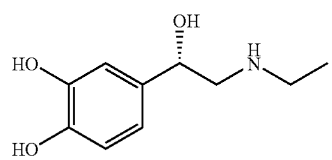 | Anti-angiogenic |
| (S)-N-n-propylnoradrenaline (>99% optically pure) | 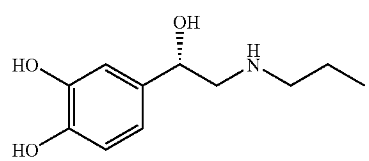 | Anti-angiogenic |
| (S)-N-n-butylnoradrenaline (>99% optically pure) | 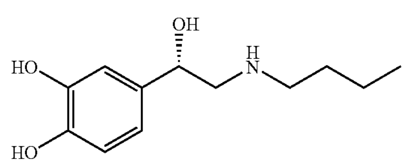 [SMILES: CCCCNC[C@@H](O)c1ccc(O)c(O)c1] | Anti-angiogenic |
| (R,S)-N-tert-butylnoradrenaline (Colterol) (racemate) | 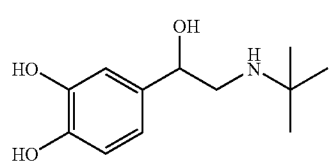 [SMILES: CC(C)(C)NCC(O)c1ccc(O)c(O)c1] | Anti-angiogenic |

TABLE 1A-continued

Anti-angiogenicity of compounds of present invention.

| Compound (measured at 20 µM) | Structure | Activity |
|---|---|---|
| 1-(3,4-dihydroxyphenyl)-2-(Isopropylamino)-1(R,S)-butanol (Isoetharine) (racemate) | 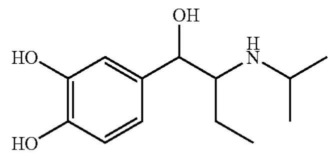 [SMILES: CCC(NC(C)C)C(O)c1ccc(O)c(O)c1] | Anti-angiogenic |
| (S)-1-(N-isopropyl)-3-methoxydopamine | 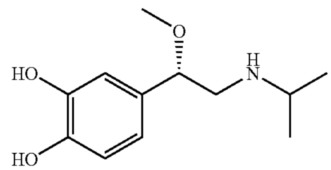 [SMILES: CO[C@H](CNC(C)C)c1ccc(O)c(O)c1] | Anti-angiogenic |
| (R)-1-(N-isopropyl)-3-methoxydopamine | 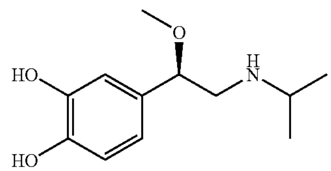 [SMILES: CO[C@@H](CNC(C)C)c1ccc(O)c(O)c1] | Anti-angiogenic |

TABLE 1B

Dopamine and catecholamines that do not exhibit anti-angiogenic properties.

| Compound (measured at 20 µM) | Structure | Activity |
|---|---|---|
| Dopamine | 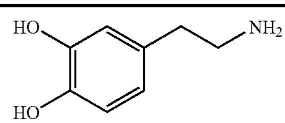 | Anti-angiogenic[b] |
| (S)-Noradrenaline (99.06 ± 0.01% optically pure) | 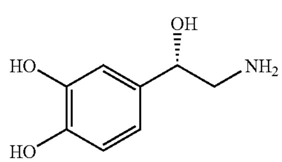 [SMILES: NC[C@@H](O)c1ccc(O)c(O)c1] | Non-antiangiogenic |
| (R)-Noradrenaline | 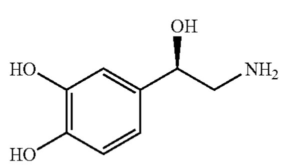 [SMILES: NC[C@H](O)c1ccc(O)c(O)c1] | Angiogenic[a] |
| (R,S)-Adrenaline | 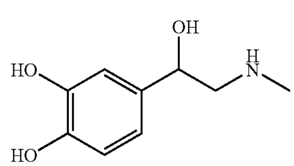 | Angiogenic[a] Non-antiinvasive |
| (R,S)-isoproterenol | 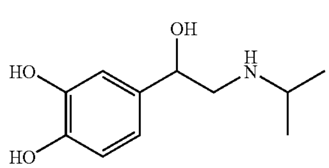 | Non-antiangiogenic |

TABLE 1B-continued

Dopamine and catecholamines that do not exhibit anti-angiogenic properties.

| Compound (measured at 20 μM) | Structure | Activity |
|---|---|---|
| (R)-isoproterenol | [structure: 3,4-dihydroxyphenyl-CH(OH)-CH2-NH-CH(CH3)2] | Angiogenic[a] Non-antiinvasive |

[a]Ref. Thaker et al., 2006.
[b]Ref. Basu et al., 2001.

Figure 9:
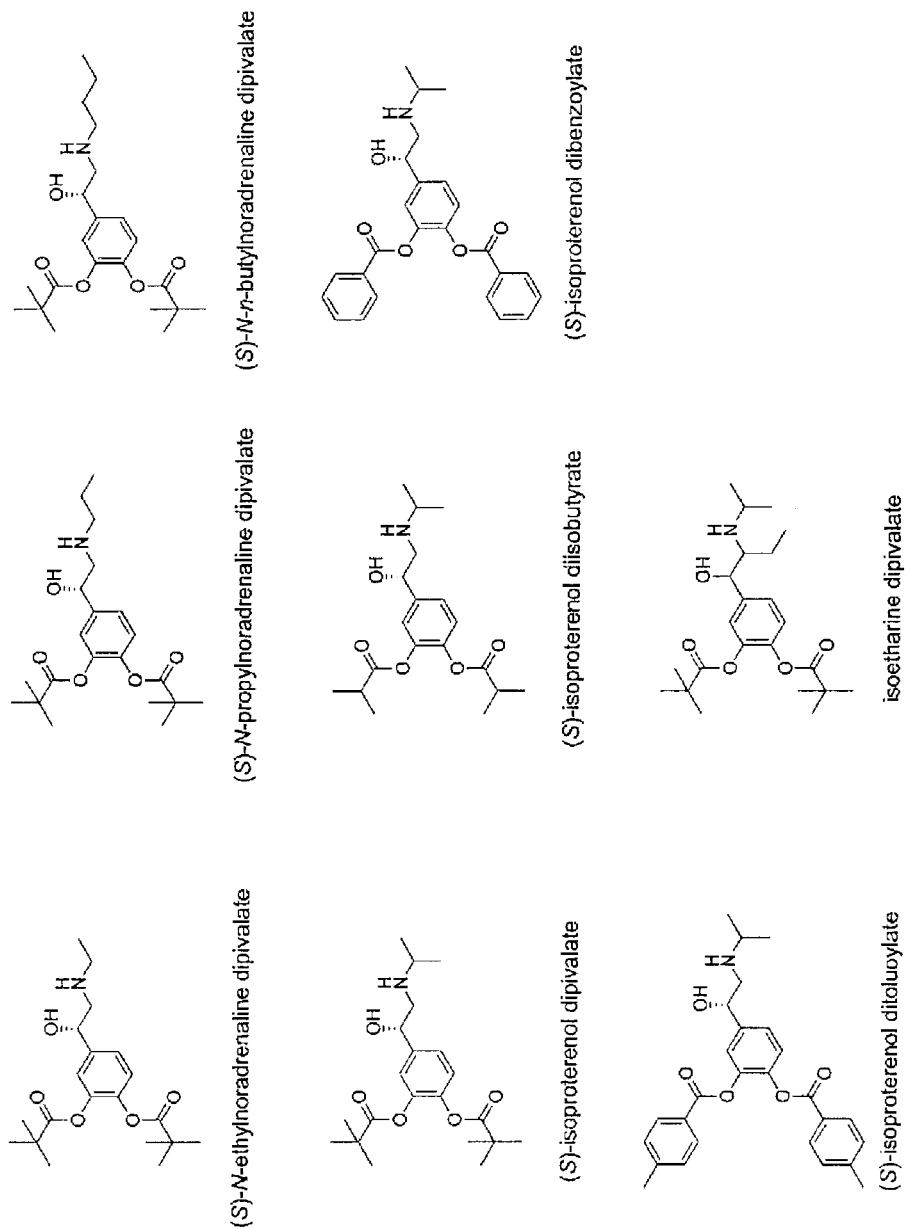
Figure 10:
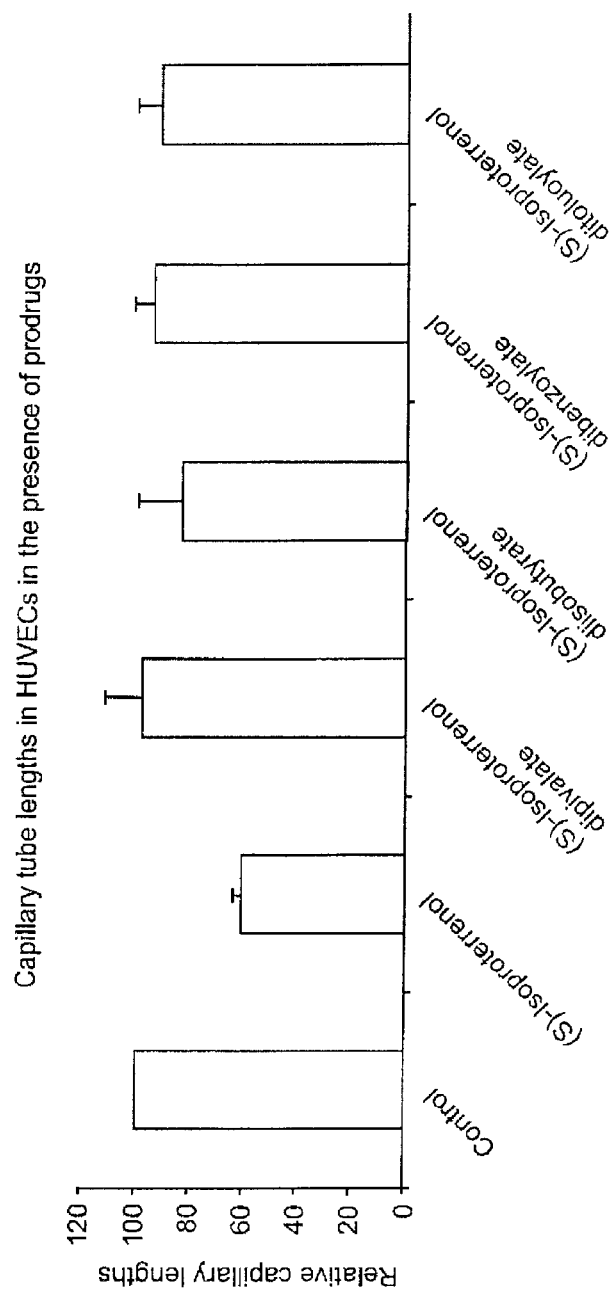
FIG. 10. Anti-angiogenic activity of (S)-isoproterenol and some of its prodrugs were measured by in vitro Matrigel endothelial cell capillary-tube formation assay. HUVECs were cultured on Matrigel™ in the absence (control) and in the presence of (S)-isoproterenol, (S)-isoproterenol dipivalate, (S)-isoproterenol diisobutyrate, (S)-isoproterenol dibenzoylate and (S)-isoproterenol ditoluoylate of which concentrations were adjusted to 20 µM. After 22 h of incubation, two randomly selected microscopic fields were photographed for each cell culture. The total length of tube structures of HUVECs in each photograph was measured using ImageJ™ free software and normalized with that of control culture. The averaged data with standard deviation are shown.

Since (S)-isoproterenol and its analogs are anti-glycation agents (Yeboah et al., 2005) and we have now found that they are anti-angiogenic, these activities may show synergy effects when both glycation and angiogenesis are contributing to the disease, for example diabetic retinopathy. For such applications, the compounds and their prodrugs with anti-glycation activity and anti-angiogenic activity, but lacking adrenergic activity are preferred. More specifically, (S)-isoproterenol and its prodrugs are in particular interest. Some prodrugs listed in FIG. 9 are (S)—N-ethyladrenaline dipivalate, (S)—N-propylnoradrenaline dipivalate, (S)—N-n-butylnoradrenaline dipivalate, (S)-isoproterenol dipivalate, (S)-isoproterenol diisobutyrate, (S)-isoproterenol dibenzoylate, (S)-isoproterenol ditoluoylate, and isoetharine dipivalate. Anti-angiogenic activity was measured on some prodrugs, resulting in no or weak anti-angiogenic activity as shown in FIG. 10. Considering that a part of some prodrugs may be hydrolyzed to anti-angiogenic (S)-isoproterenol during 22 hrs of the incubation period, the prodrugs in FIG. 11 may be non-anti-angiogenic or very weak anti-angiogenic agents.

Tumor cell invasion is a process involved in the late stage of cancer development where tumor migrates from one tissue to other tissues. The present invention provides a novel activity of (S)-isoproterenol to prevent tumor cell invasion. FIG. 3 shows that (S)-isoproterenol (20 μM) reduced the invasion of HUVECs in Matrigel by 60%. In contrast, its optical isomer (R)-isoproterenol did not show any anti-invasion activity. Together with anti-angiogenic activity, (S)-isoproterenol has dual activities to treat tumor metastasis.

The present Invention excludes the use of the compounds with β2-adrenergic agonist activity such as (R)-isoproterenol as β2-adrenergic agonists are angiogenic (Thaker et al., 2006), unless anti-angiogenic activity of the ingredients exceeds the angiogenic activity of the β2-adrenergic agonist component(s) and the β2-adrenergic activity does not interfere the therapeutic effects of the present invention and does not provide adrenergic adverse effects.

The present invention includes the use of prodrugs of (S)-isoproterenol and its analogs, where the aromatic hydroxyl group(s) are modified. The prodrugs may enhance and accelerate the tissue absorption and penetration due to its high lipophilicity. The prodrugs also protect the aromatic hydroxyl group(s) from chemical reactions such as oxidation during storage. The prodrugs are also less UV-light sensitive compared with the corresponding drugs.

In case that a high optical purity is desired for anti-angiogenic activity and for minimizing adverse adrenergic effects, prodrugs reduce the racemization during storage. Table 2 describes the optical purities of (S)-isoproterenol and (S)-isoproterenol dipivalate after incubation in various eye drop formulations for 10 days at 55° C. and compared with those before incubation. The incubation for 10 days at 55° C. corresponds to the incubation for 167 days at 22° C.

Figure 8:
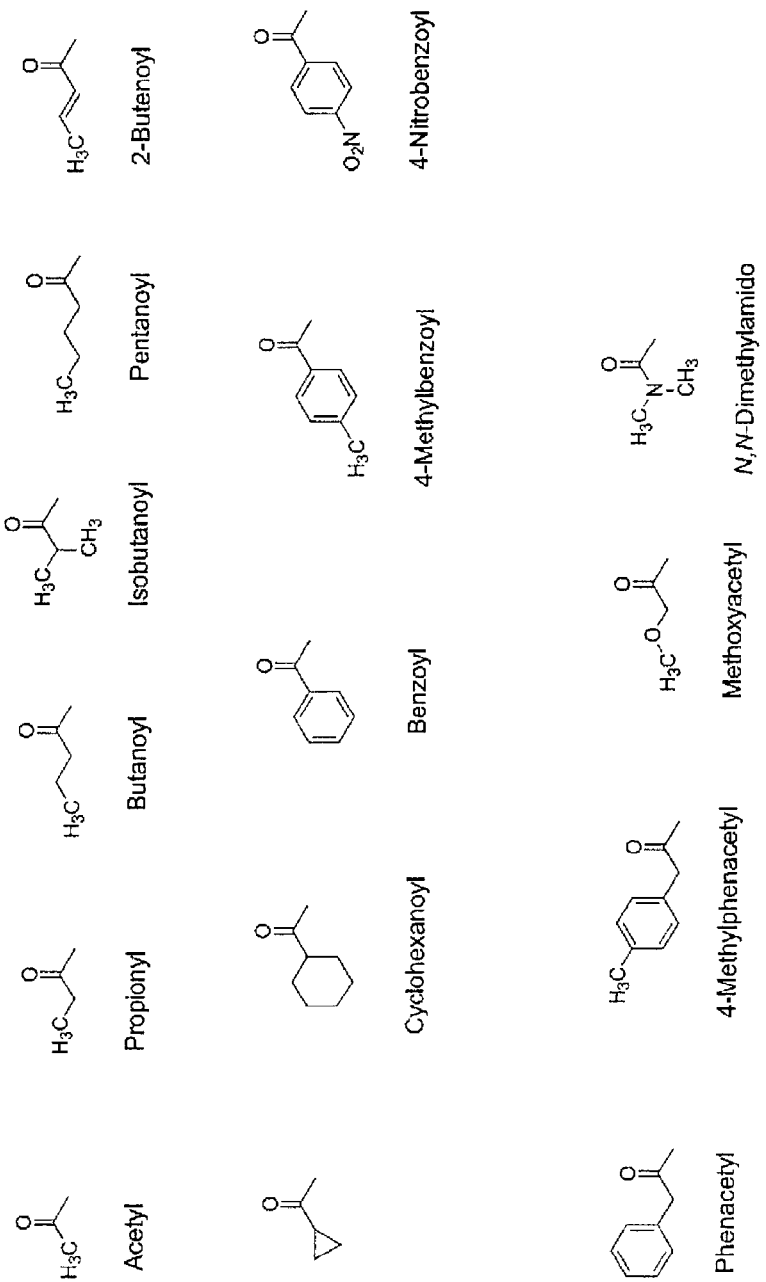
FIG. 8. Chemical structures of some protecting groups of the aromatic dihydroxyl groups of compounds of the present invention FIG. 9. Chemical structures of some prodrugs useful in the present invention.

The average optical purity of (S)-isoproterenol after incubating 10 days at 55° C. was 97.35±0.52%, resulting in conversion of 2.55% of (S)-isoproterenol to (R)-isoproterenol. This corresponds to a reduction of optical purity of (S)-isoproterenol from 99.90% to 90% after 655 days of storage at room temperature. On the contrary, the average optical purity of (S)-isoproterenol dipivalate after incubating 10 days at 55° C. was approximately 99.85±0.08%, resulting in 0.02% of (S)-isoproterenol dipivalate conversion to the corresponding (R)-isoform. This implies that the optical purity of (S)-isoproterenol dipivalate is reduced from 99.87% to 99.78% after 2 years of storage at room temperature. Since a high optical purity of (S)-isoproterenol is greatly desired for anti-angiogenic activity, prodrug formulation is preferred. Prodrug formulation is not limited to pivalate esters. Examples of some protecting groups of the aromatic hydroxyl groups are listed in FIG. 8.

TABLE 2

Optical stability of (S)-isoproterenol after 10 days of storage at 55° C.

| Ingredients | Concentrations of inactive ingredients and optical purity of (S)-isoproterenol (1.7 mg/mL) | | | |
|---|---|---|---|---|
| (S)-isoproterenol[a] (% optical purity) | 97.90% | 97.26% | 97.56% | 96.68% |
| Povidone | 2 mg/mL | 2 mg/mL | 2 mg/mL | — |
| NaCl | — | 8 mg/mL | — | 8 mg/mL |
| Benzalkonium chloride | 0.04 mg/mL | 0.04 mg/mL | — | 0.04 mg/mL |
| D-Mannitol | 54.7 mg/mL | — | 54.7 mg/mL | — |
| Chlorobutanol | — | — | 1 mg/mL | — |
| Tween ™ 80 | — | — | — | 2.5 mg/mL |
| 2-hydroxypropyl cyclodextrin | — | 10.1 mg/mL | 10.1 mg/mL | — |
| pH | 6.0 | 6.0 | 6.0 | 6.0 |

[a]The optical purity of the starting material was 99.90%.

TABLE 3

Optical stability of (S)-isoproterenol dipivalate after 10 days of storage at 55° C.

| Ingredients | Concentrations of inactive ingredients and optical purity of (S)-isoproterenol (3.0 mg/mL) | | | |
|---|---|---|---|---|
| (S)-isoproterenol dipivalate[a] (% optical purity) | 99.90% | 99.86% | 99.74% | >99.90% |
| Povidone | 2 mg/mL | 2 mg/mL | 2 mg/mL | — |
| NaCl | — | 8 mg/mL | — | 8 mg/mL |
| Benzalkonium chloride | 0.04 mg/mL | 0.04 mg/mL | — | 0.04 mg/mL |
| D-Mannitol | 54.7 mg/mL | — | 54.7 mg/mL | — |
| Chlorobutanol | — | — | 1 mg/mL | — |
| Tween ™ 80 | — | — | — | 2.5 mg/mL |
| 2-hydroxypropyl cyclodextrin | — | 10.1 mg/mL | 10.1 mg/mL | — |
| pH | 6.0 | 6.0 | 6.0 | 6.0 |

[a]The optical purity of the starting material was 99.87%.

Streptozotocin was used to induce diabetes in rats. The blood glucose levels were monitored once a week over a 27 week period for non-diabetic and diabetic rats. Control, Group I (receiving vehicle) and Group II (receiving prodrug) of non-diabetic animals (filled diamond) have a steady blood glucose level of 5.1±0.4 and 5.1±0.4 mM, respectively). An increase in blood glucose levels was noted for Group III (receiving vehicle) and Group IV (receiving prodrug) diabetic rats, during the first 2 weeks of diabetes induction. The glucose levels then stabilized at 28±4 and 27±5 mM, respectively. As the glucose level at around 5 mM is considered normal, rats in Group I and Group II are non-diabetic. Rats are considered diabetic when the blood glucose level exceeds 15 mM. Thus, all of the rats in Group III and Group IV are diabetic. The consistency of the blood glucose level between Groups I and II and between Groups III and IV shows that (S)-isoproterenol does not affect the blood glucose level and diabetes.

Figure 5A:
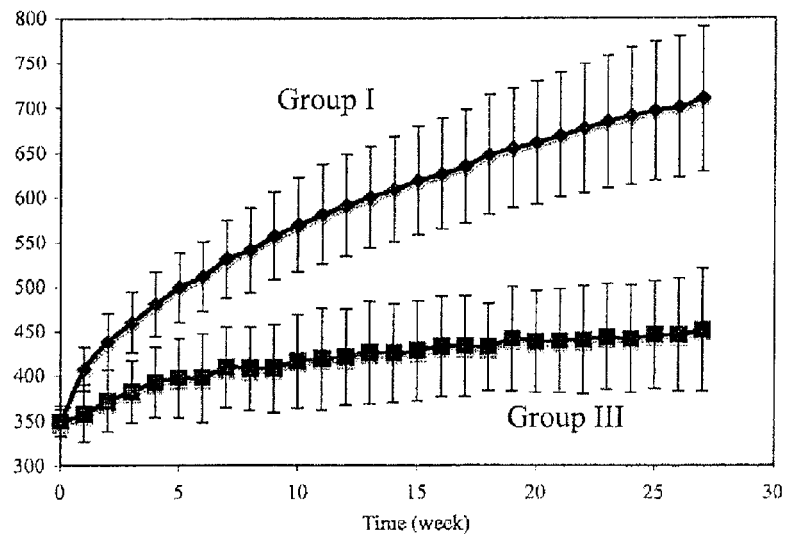
FIG. 5. Average body weight of rats over the period of the experiment. Normal (filled diamond) or diabetic (filled squares) rats receiving vehicle (A) or (S)-isoproterenol dipivalate eye drop (B) were weighed weekly.
Figure 5B:
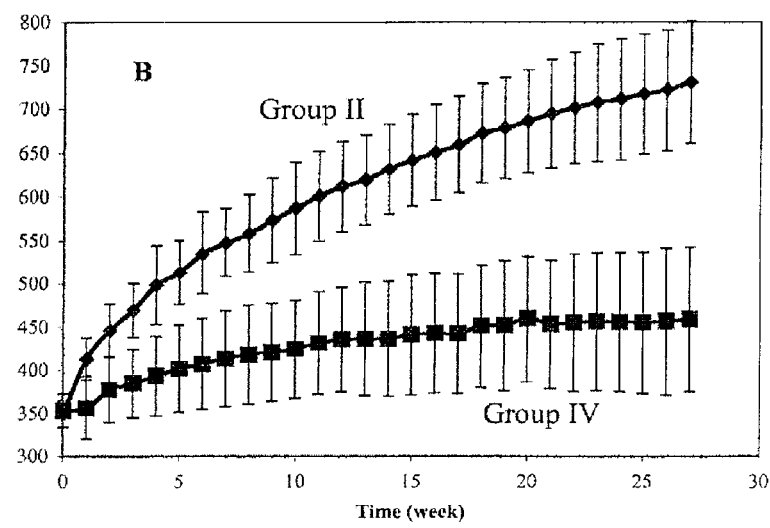

Another potential adverse effect of (S)-isoproterenol on body weight loss/gain was monitored. The weight gain during the experiments is essentially the same between Group I (non-diabetic rats receiving vehicle) in FIG. 5A and Group II (non-diabetic rats receiving prodrug) in FIG. 5B, suggesting that no effect of (S)-isoproterenol in weight gain/loss of non-diabetic rats. The weight gain is much less in the diabetic rats compared to those of non-diabetic rats (Chen et al., 2004); however, the weight gain of Group III (diabetic rats receiving vehicle) in FIG. 5A is essentially the same as that of Group IV (diabetic rats receiving prodrug) in FIG. 5B, showing no effect of (S)-isoproterenol in weight gain/loss of diabetic rats.

Figure 6:
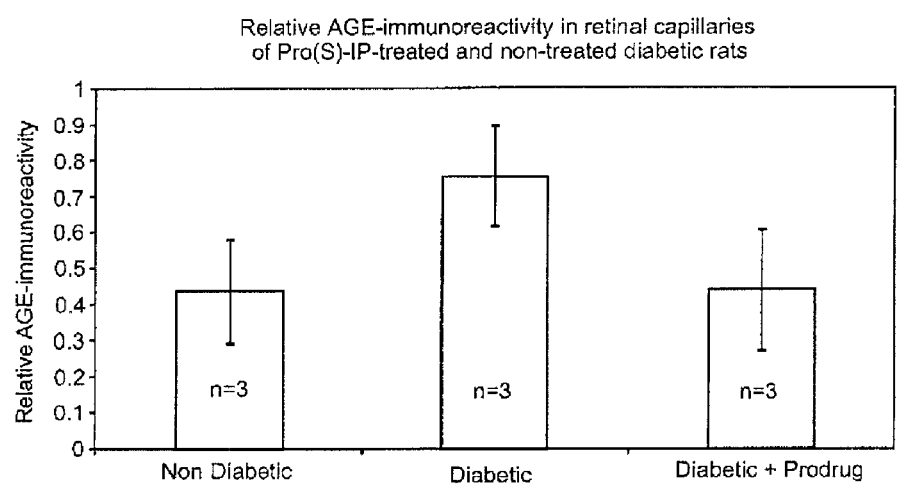
FIG. 6. Quantitative glycation of retinal capillaries as the glycated capillary densities in red fluorescence are normalized by the total retinal capillary density in non-diabetic rats, diabetic rats with vehicle, and diabetic rats with 0.1% (S)-isoproterenol dipivalate eye drop treatment. The P values are 0.052 and 0.068 for non-diabetic rats vs. diabetic rats with vehicle and diabetic rats with (S)-isoproterenol dipivalate treatment vs. diabetic rats with vehicle, respectively. It should be noticed that acellular capillaries, which are enriched in diabetic retina with no (S)-isoproterenol dipivalate treatment, are likely highly glycated and would reduce the above P values further. "n" is the number of the eyes used in the analysis.

While rats are not an appropriate model organism for studying anti-angiogenicity directly, they may be used to study the ability of a drug to penetrate to the retina of an eye. It is known that (S)-Isoproterenol is a potent anti-glycation agent (Yeboah et al., 2005). The delivery of (S)-isoproterenol into the retina was demonstrated by inhibiting retinal glycation with (S)-isoproterenol dipivalate eye drops. Antibodies against glycated bovine serum albumin stained glycated retinal proteins in red fluorescence. The glycation of retinal capillaries was evaluated by superimposing the red fluorescence of anti-glycation antibodies with the above green fluorescence of anti-lectin antibodies, resulting green to light orange fluorescence of healthy retinal capillaries with less glycation and red fluorescence of highly glycated retinal capillaries. The retinal capillaries of non-diabetic rat eyes with least glycation showed green to light orange fluorescence. Similar healthy capillaries were observed in diabetic rat eye with (S)-isoproterenol dipivalate. The retinal capillaries in diabetic rat eye with vehicle were stained in red fluorescence and were also damaged as less number of capillaries were stained. FIG. 6 quantifies the effect by normalizing the red fluorescence intensity of AGEs by the retinal capillary density, resulting 0.43±0.15, 0.44±0.17, and 0.76±0.14 for non-diabetic rats, diabetic rats with (S)-isoproterenol dipivalate treatment, and diabetic rats with vehicle, respectively. The P values are 0.052, 0.068, and 0.971 for non-diabetic rats vs. diabetic rats with vehicle, diabetic rats with (S)-isoproterenol dipivalate vs. diabetic rats with vehicle, and non-diabetic rats vs. diabetic rats with (S)-isoproterenol dipivalate, respectively. It should be noticed that acellular capillaries, which are enriched in diabetic retina with vehicle, are expected to be highly glycated such that the degree of glycation for diabetic rats with vehicle would be greater than 0.76±0.14 in FIG. 6, demonstrating that (S)-isoproterenol dipivalate effectively delivered (S)-isoproterenol into retina and significantly reduced the glycation in retinal capillaries. Since (S)-isoproterenol can be effectively delivered to the retina of an eye where it can exert its anti-angiogenic effect, it is expected to be useful in the treatment and/or prevention of diabetic retinopathy.

In one preferred embodiment, the present invention provides a novel use of (S)-isoforms of isoproterenol and its analogs, for preventing and/or treating diseases related to angiogenesis and/or invasion. These compounds satisfy several criteria important for this application. First of all, the anti-angiogenic activity of (S)-isoproterenol and its analogs is high. The anti-angiogenic activity at cellular level must be observable at or below 1 mM, preferably at or below 100 μM, more preferably at or below 20 μM. Secondly, the adrenergic activity, which is characteristic of the (R)-isoform is insignificant for the (S)-isoform. The adrenergic activities of the (S)-isoform of adrenalines are much lower that that of the corresponding (R)-isoform (Patil et al., 1974). In particular, topical administration of up to 20% (S)-isoproterenol hydrochloride did not show any indication to lower intra-ocular pressure in the human eye (Kass et al., 1976).

The (S)-isoform of isoproterenol and its analogs are considered to be adrenergically inert and be safe for topical and systemic administration. The evidence that most commercial drugs of adrenergic agonists are racemic mixtures provides strong practical reason for the inertness of the (S)-isomers (Boulton & Fawcett, 2002). Preparations according to one preferred embodiment of the present invention contain only the (S)-isoform of isoproterenol and its analogs in order to reduce potential adverse effects through stimulation of adrenergic receptors.

Isoproterenol is known to have a duration long enough for a reasonable frequency of administration such as a twice-a-day administration, e.g., when 2.47% (R,S)-isoproterenol was instilled to normal human eyes a 20% reduction in ocular tension was observed, lasting at least 12 h (Ross & Drance, 1970).

Once (S)-isoproterenol gets into blood circulation system, it is metabolized to 3-methyl-(S)-isoproterenol and its plasma half-life is in the range from 3.0 to 4.1 min (Conway et al., 1968), minimizing the possibility of any systemic adverse effects of (S)-isoproterenol.

REFERENCES

The contents of the entirety of each of which are incorporated by this reference.

Basu, S.; Nagy, J. A.; Pal, S.; Vasile, E.; Eckelhoefer, I. A.; Bliss, V. S.; Manseau, E. J.; Dasgupta, P. S.; Dvorak, H. F.; Mukhopadhyay, D. The neurotransmitter dopamine inhibits angiogenesis induced by vascular permeability factor/vascular endothelial growth factor. *Nat. Med.* (2001), 7, 569-574.

Bentley, G. A.; Starr, J. The antinociceptive action of some β-adrenoceptor agonists in mice. *Br. J. Pharmacol.* (1986) 88, 515-521.

Boulton, D. W.; Fawcett, J. P. β2-Agonist eutomers: A rational option for the treatment of asthma? *Am. J. Respir. Med.* (2002), 1, 305-311.

Chen, A. S.; Taguchi, T.; Sugiura, M.; Wakasugi, Y.; Kamei, A.; Wang, M. W.; Miwa, I. Pyridoxal-aminoguanidine adduct is more effective than aminoguanidine in preventing neuropathy and cataract in diabetic rats. *Horm. Metab. Res.* (2004) 36, 183-187.

Conway, W. D.; Minatorya, H.; Lnds, A. M.; Shekosky, J. M. Absorption and elimination profile of isoproterenol III. The metabolic fate of dl-isoproterenol-7-3H in the dog. *J. Pharm. Sci.* (1968) 57, 1135-1141.

Chalothorn, D.; Zhang, H.; Clayton, J. A.; Thomas, S. A.; Faber, J. E. Catecholamines augment collateral vessel growth and angiogenesis in hindlimb ischemia. *Am. J. Physiol. Heart Circ. Physiol.* (2005) 289, H947-H959.

Dejgaard, A.; Hilsted, J.; Christensen, N. J. Noradrenaline and isoproterenol kinetics in diabetic patients with and without autonomic neuropathy. *Diabetologia.* (1986) 29, 773-777.

Jarvinen, T.; Jarvinen, K. Prodrugs for improved ocular drug delivery. *Adv. Drug Delivery Rev.* (1996), 19, 203-224.

Kass, M. A.; Reid, T. W.; Neufeld, A. H.; Bausher, L. P.; Sears, M. L. The effect of d-isoproterenol on intraocular pressure of the rabbit, monkey, and man. *Invest. Ophthalmol.* (1976), 15, 113-118.

Kyselova, Z.; Stefek, M.; Bauer, V. Pharmacological prevention of diabetic cataract. *J. Diabetes Complications.* (2004) 18, 129-140.

Lands, A. M.; Luduena, F. P.; Tuner, B. F. The pharmacologic activity of the optical isomers of isoproterenol compared with that of the optically inactive analog 1-(3,4-dihydroxyphenyl)-2-isopropylaminoethane HCl. *J. Pharmacol. Exp. Ther.* (1954), 111, 469-474.

Mandell, A. I.; Stentz, F.; Kitabchi, A. E. Dipivalyl epinephrine: a new pro-drug in the treatment of glaucoma. *Ophthalmology.* (1978) 85, 268-275.

Muilick, A.; Konishi, Y. Anti-diabetic cataract compounds and their uses. International Publication Number WO 2007/109882, Oct. 4, 2007.

Patil, P. N.; Miller, D. D.; Trendelenburg U. Molecular geometry and adrenergic drug activity. *Pharmacol. Rev.* (1974), 26, 323-392.

Ross, R. A.; Drance, S. M. Effects of topically applied isoproterenol on aqueous dynamics in man. *Arch. Ophthal.* (1970) 83, 39-46.

Seidehamel, R. J.; Dungan, K. W.; Hickey, T. E. Specific hypotensive and antihypertensive ocular effects of d-isoproterenol in rabbits. *Am. J. Ophthalmol.* (1975), 79, 1018-1025.

Thaker, P. H.; Han, L. Y.; Kamat, A. A.; Arevalo, J. M.; Takahashi, R.; Lu, C.; Jennings, N. B.; Armaiz-Pena, G.; Bankson, J. A.; Ravoori, M.; Merritt, W. M.; Lin, Y. G.; Mangala, L. S.; Kim, T. J.; Coleman, R. L.; Landen, C. N.; Yang Li, Y.; Felix, E.; Sanguino, A. M.; Newman, R. A.; Lloyd, M.; Gershenson, D. M.; Kundra, V.; Lopez-Berestein, G.; Lutgendorf, S. K.; Cole, S. W.; Sood, A. K. Chronic stress promotes tumor growth and angiogenesis in a mouse model of ovarian carcinoma. *Nat. Med.* (2006), 12, 939-944.

Walker, S. B.; Kradjan, W. A.; Bierman, C. W. Bitolterol mesylate: a beta-adrenergic agent. Chemistry, pharmacokinetics, pharmacodynamics, adverse effects and clinical efficacy in asthma. *Pharmacotherapy* (1985), 5, 127-137.

Wang, B. C.; Bloxham, D. D.; Goetz, K. L. Effect of dipivalyl derivatives of catecholamines on cardiovascular function in the conscious dog. *J. Pharmacol. Exp. Ther.* (1977) 203, 442-448.

Yeboah, F.; Konishi, Y.; Cho, S. J.; Lertvorachon, J.; Kiyota, T.; Popek, T. Anti-glycation agents for preventing age-, diabetes-, and smoking-related complications. US Patent Publication 2005/0043408, Feb. 24, 2005.

Other advantages that are inherent to the structure are obvious to one skilled in the art. The embodiments are described herein illustratively and are not meant to limit the scope of the invention as claimed. Variations of the foregoing embodiments will be evident to a person of ordinary skill and are intended by the inventor to be encompassed by the following claims.

The invention claimed is:

1. A method of inhibiting angiogenesis in a human subject in need of such inhibition,
    comprising administering to the human subject an anti-angiogenic effective amount of a compound selected from the group consisting of (S)-isoproterenol, (S)—N-ethylnoradrenaline, (S)—N-n-propylnoradrenaline, (S)—N-n-butylnoradrenaline, (R,S)—N-tert-butylnoradrenaline, 1-(3,4-dihydroxyphenyl)-2-(isopropylamino)-1(R,S)-butanol, (S)-1-(N-isopropyl)-3-methoxydopamine, and (R)-1-(N-isopropyl)-3-methoxydopamine, or
    a physiologically tolerated salt thereof, or any mixture of the compounds of formula (I) as an anti-angiogenic agent.

2. The method according to claim 1, wherein the compound has an optical purity of 95% or greater.

3. The method according to claim 1, wherein the compound has an optical purity of 97% or greater.

4. The method according to claim 1, wherein the compound has an optical purity of 99% or greater.

5. The method according to claim 1, wherein the compound is (S)-isoproterenol or (S)-isoproterenol dipivalate.

6. The method according to claim 1, wherein the compound is (S)-1-(N-isopropyl)-3-methoxydopamine or (R)-1-(N-isopropyl)-3-methoxydopamine.

7. The method according to claim 1, wherein the compound is (S)—N-ethylnoradrenaline dipivalate, (S)—N-n-propylnoradrenaline dipivalate, (S)—N-n-butylnoradrenaline dipivalate, (S)-isoproterenol dipivalate, (S)-isoproterenol diisobutyrate, (S)-isoproterenol dibenzoylate, (S)-isoproterenol ditoluoylate or 1-(3,4-dihydroxyphenyl)-2-(isopropylamino)-1(R,S)-butanol dipivalate.

8. The method according to claim 1, wherein the human subject suffers from diabetic retinopathy, diabetic macular edema, or age-related macular degeneration.

* * * * *